United States Patent
Horiuchi et al.

(10) Patent No.: US 9,318,712 B2
(45) Date of Patent: Apr. 19, 2016

(54) XANTHONE COMPOUND AND ORGANIC LIGHT-EMITTING DEVICE INCLUDING THE SAME

(75) Inventors: Takayuki Horiuchi, Tokyo (JP); Jun Kamatani, Tokyo (JP); Naoki Yamada, Inagi (JP); Kengo Kishino, Tokyo (JP); Kenichi Ikari, Abiko (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 322 days.

(21) Appl. No.: 13/882,978

(22) PCT Filed: Oct. 17, 2011

(86) PCT No.: PCT/JP2011/074371
§ 371 (c)(1),
(2), (4) Date: May 1, 2013

(87) PCT Pub. No.: WO2012/060234
PCT Pub. Date: May 10, 2012

(65) Prior Publication Data
US 2013/0214268 A1    Aug. 22, 2013

(30) Foreign Application Priority Data

Nov. 4, 2010 (JP) ................................ 2010-247857

(51) Int. Cl.
| | |
|---|---|
| *H01L 51/50* | (2006.01) |
| *H01L 51/00* | (2006.01) |
| *C07D 311/86* | (2006.01) |
| *C07D 409/14* | (2006.01) |
| *H01L 51/52* | (2006.01) |
| *C09K 11/06* | (2006.01) |
| *H05B 33/22* | (2006.01) |

(52) U.S. Cl.
CPC .......... *H01L 51/0074* (2013.01); *C07D 311/86* (2013.01); *C07D 409/14* (2013.01); *C09K 11/06* (2013.01); *H01L 51/0073* (2013.01); *H01L 51/5203* (2013.01); *H05B 33/22* (2013.01); *C09K 2211/1088* (2013.01); *C09K 2211/1092* (2013.01); *H01L 51/006* (2013.01); *H01L 51/0072* (2013.01); *H01L 51/0085* (2013.01); *H01L 51/5016* (2013.01); *H01L 51/5048* (2013.01); *H01L 51/5092* (2013.01)

(58) Field of Classification Search
USPC ........................................................ 549/392
See application file for complete search history.

(56) References Cited

U.S. PATENT DOCUMENTS

| | | | |
|---|---|---|---|
| 6,310,360 B1 | 10/2001 | Forrest et al. | |
| 2002/0074935 A1 | 6/2002 | Kwong et al. | |
| 2003/0072964 A1 | 4/2003 | Kwong et al. | |
| 2007/0231601 A1 | 10/2007 | Nakasu et al. | |
| 2009/0066226 A1* | 3/2009 | Sugita et al. | 313/504 |
| 2012/0085997 A1* | 4/2012 | Sugita et al. | 257/40 |

FOREIGN PATENT DOCUMENTS

| | | | |
|---|---|---|---|
| DE | 4211420 A1 * | 10/1993 | .......... C07D 493/04 |
| WO | 2006/114966 A1 | 11/2006 | |
| WO | 2009024087A A1 | 2/2009 | |
| WO | 2011/136156 A1 | 11/2011 | |
| WO | WO2011136156 A1 | 11/2011 | |

OTHER PUBLICATIONS

M.Sousa et al., "Synthesis of Xanthones: An Overview", Current Medicinal Chemistry 2005, vol. 12, No. 21, Oct. 1, 2005, pp. 2447-2479, XP55104428 Bentham Science Publishers Ltd.
Howard M. Coquhoun et al., "Synthesis of Dixanthones and Poly(dixanthone)s by Cyclization of 2-Aryloxybenzonitriles in Trifluoromethanesulfonic Acid", Organic Letters, Jul. 26, 2001, pp. 2337-2340, XP55104475.
Datebase CAPLUS on STN AN 2001, pp. 2337-2340, H.M.et al.
Datebase CAPLUS on STN AN 1965, pp. 2539-2611, Schoenberg, A. et al.
Merkel et al., "Thermodynamic energies of donor and acceptor triplet states", Journal of Photochemistry and Photobiology A:Chemistry, vol. 193, pp. 110-121, 2008.

* cited by examiner

*Primary Examiner* — Jennifer Chriss
*Assistant Examiner* — Dylan Kershner
(74) *Attorney, Agent, or Firm* — Canon USA Inc. IP Division

(57) ABSTRACT

An organic light-emitting device that realizes high-emission efficiency and low-driving voltage is provided. The organic light-emitting device contains a xanthone compound represented by general formula [1].

11 Claims, 1 Drawing Sheet

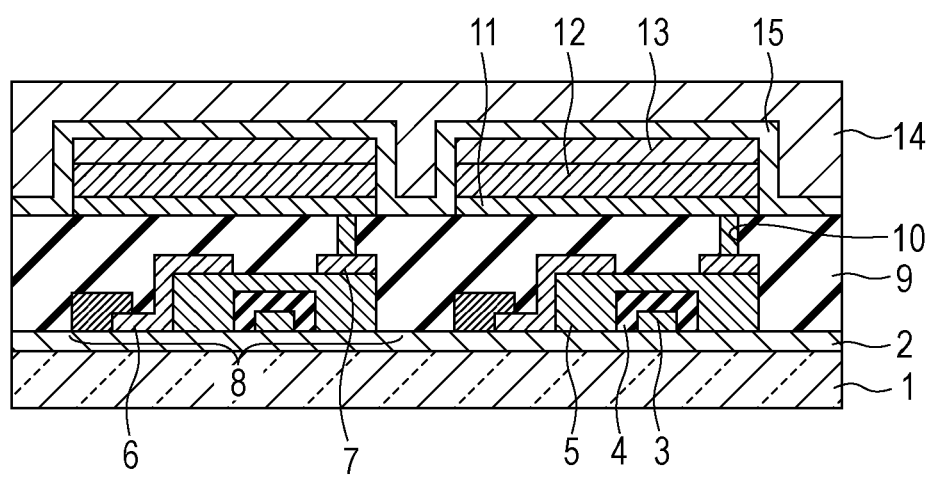

XANTHONE COMPOUND AND ORGANIC LIGHT-EMITTING DEVICE INCLUDING THE SAME

TECHNICAL FIELD

The present invention relates to a xanthone compound and an organic light-emitting device including the xanthone compound.

BACKGROUND ART

An organic light-emitting device is a device that includes an anode, a cathode, and an organic compound layer interposed between the anode and the cathode. Holes and electrons injected from the respective electrodes of the organic light-emitting device are recombined in the organic compound layer to generate excitons and light is emitted as the excitons return to their ground state. The organic light-emitting device is also called an organic electroluminescent device or organic EL device. Recent years have seen remarkable advances in the field of organic light-emitting devices. Organic light-emitting devices now feature low driving voltage, various emission wavelengths, rapid response, small thickness, and light-weightiness.

Phosphorescence-emitting devices are a type of device that includes an organic compound layer containing a phosphorescent material, with triplet excitons contributing to emission. Creation of novel organic compounds has been actively pursued to provide high-performance phosphorescence-emitting devices.

For example, PTL 1 discloses a compound 1 which is a xanthone derivative having carbazolyl groups. The compound 1 is used as a host material of a blue or green light-emitting layer of a phosphorescence-emitting device.

[Chem. 1]

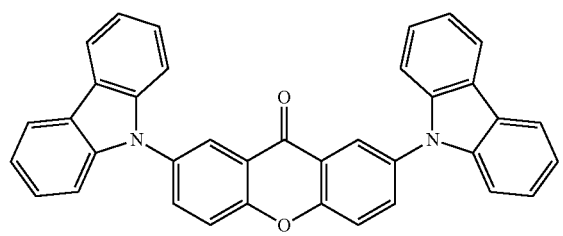

Compound 1

CITATION LIST

Patent Literatures

PTL 1 International Publication No. 2006/114966

SUMMARY OF INVENTION

Since the lowest excited triplet ($T_1$) energy of the compound described in PTL 1 is low, this material is not sufficient for a host material of an emission layer of a blue or green phosphorescence-emitting device or as a material for forming a carrier transport layer adjacent to the emission layer.

When the $T_1$ energy of the host material of the emission layer is low, the energy does not sufficiently migrate to the guest material of the emission layer and thus a sufficiently high emission is rarely achieved.

When the $T_1$ energy of the carrier transport layer adjacent to the emission layer is low, migration of the energy from the emission layer to the adjacent layer is rarely suppressed.

Accordingly, it is advantageous to provide a xanthone compound that has a high $T_1$ energy and good electron injectability. An organic light-emitting device that contains the xanthone compound and has a high emission efficiency and a low driving voltage is also provided.

The present invention provides a xanthone compound represented by general formula [1] below:

[Chem. 2]

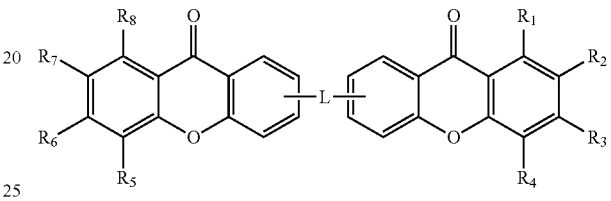

[1]

where $R_1$ to $R_8$ are each independently selected from a hydrogen atom, an alkyl group having 1 to 4 carbon atoms, a substituted or unsubstituted phenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted chrysenyl group, a substituted or unsubstituted dibenzofuranyl group, and a substituted or unsubstituted dibenzothienyl group; and L represents a single bond, a substituted or unsubstituted divalent benzene, a substituted or unsubstituted divalent biphenyl, a substituted or unsubstituted divalent terphenyl, a substituted or unsubstituted divalent naphthalene, a substituted or unsubstituted divalent phenanthrene, a substituted or unsubstituted divalent fluorene, a substituted or unsubstituted divalent triphenylene, a substituted or unsubstituted divalent chrysene, a substituted or unsubstituted divalent dibenzofuran, or a substituted or unsubstituted divalent dibenzothiophene, wherein the benzene, the biphenyl, the terphenyl, the naphthalene, the phenanthrene, the fluorene, the triphenylene, the chrysene, the dibenzofuran, and the dibenzothiophene may have an alkyl group having 1 to 4 carbon atoms as a substituent.

According to the present invention, a xanthone compound having high $T_1$ energy and good electron injectability can be provided. An organic light-emitting device that contains this xanthone compound and has high emission efficiency and low driving voltage can also be provided.

BRIEF DESCRIPTION OF DRAWINGS

FIG. 1 is a schematic cross-sectional view of an organic light-emitting device and a switching element coupled to the organic light-emitting device.

DESCRIPTION OF EMBODIMENTS

An embodiment of the present invention provides a xanthone compound represented by general formula [1] below.

[Chem. 3]

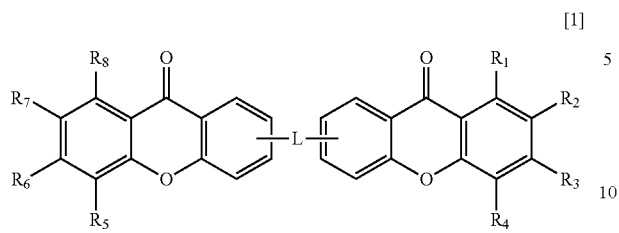

[1]

In general formula [1], $R_1$ to $R_8$ are each independently selected from a hydrogen atom, an alkyl group having 1 to 4 carbon atoms, a substituted or unsubstituted phenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted chrysenyl group, a substituted or unsubstituted dibenzofuranyl group, and a substituted or unsubstituted dibenzothienyl group.

The benzene, the biphenyl, the terphenyl, the naphthalene, the phenanthrene, the fluorene, the triphenylene, the chrysene, the dibenzofuran, and the dibenzothiophene may have an alkyl group having 1 to 4 carbon atoms as a substituent.

Examples of the alkyl group having 1 to 4 carbon atoms include a methyl group, an ethyl group, a normal propyl group, an isopropyl group, a normal butyl group, a secondary butyl group, an isobutyl group, and a tertiary butyl group.

The phenyl group, naphthyl group, phenanthryl group, fluorenyl group, triphenylenyl group, chrysenyl group, dibenzofuranyl group, and dibenzothienyl group represented by $R_1$ to $R_8$ may each further include a substituent.

Examples of such a substituent include an alkyl group having 1 to 4 carbon atoms, an aryl group such as a phenyl group, a biphenyl group, a naphthyl group, a phenanthryl group, a fluorenyl group, a chrysenyl group, and a triphenylenyl group, a dibenzofuranyl group, and a dibenzothienyl group.

L represents a single bond, a substituted or unsubstituted divalent benzene, a substituted or unsubstituted divalent biphenyl, a substituted or unsubstituted divalent terphenyl, a substituted or unsubstituted divalent naphthalene, a substituted or unsubstituted divalent phenanthrene, a substituted or unsubstituted divalent fluorene, a substituted or unsubstituted divalent triphenylene, a substituted or unsubstituted divalent chrysene, a substituted or unsubstituted divalent dibenzofuran, or a substituted or unsubstituted divalent dibenzothiophene.

When L represents a single bond, the xanthone compound represented by general formula [1] has a structure in which two xanthone skeletons are directly bonded to each other. When L represents a divalent linking group, the xanthone compound represented by general formula [1] has a structure in which two xanthone skeletons are bonded to each other through the linking group. L may include an alkyl group having 1 to 4 carbon atoms as a substituent.

Properties of the Xanthone Compound

The xanthone compound of this embodiment is a compound having two xanthone skeletons represented by structural formula A below. Herein, the structure represented by structural formula A is referred to as a "xanthone skeleton".

[Chem. 4]

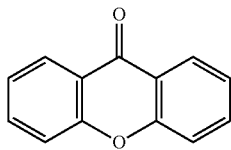

Structural formula [A]

Since the xanthone skeleton has a carbonyl group, the xanthone skeleton has high electron affinity and thus the compound has high electron injectability.

Since molecule stacking is likely to occur, electrons easily migrate between molecules in a solid state. In other words, the electron mobility is high.

Since the xanthone compound has two xanthone skeletons the xanthone compound has higher amorphousness than when only one xanthone skeleton is included. The amorphousness refers to a property of a compound in a solid state keeping an amorphous state without crystallization even when the compound is under a high temperature condition.

A compound having high amorphousness may be used in an organic compound layer of an organic light-emitting device.

The xanthone compound of this embodiment has a high lowest excited triplet ($T_1$) energy. The $T_1$ energy of the xanthone skeleton itself represented by structural formula A was measured to provide an explanation therefor.

A diluted toluene solution of the xanthone skeleton was subjected to a phosphorescent spectrum measurement under a condition of 77 K and the $T_1$ energy was estimated from the 0-0 band of that spectrum.

The result showed that the $T_1$ energy of the xanthone skeleton represented by structural formula A was 3.02 eV or 410 nm on a wavelength basis. This $T_1$ energy is higher than the blue wavelength region (440 nm or more and 480 nm or less).

The xanthone compound can have improved amorphousness by having a substituent. The substituent may be introduced to positions $R_1$ to $R_8$ in general formula [1].

The xanthone compound of this embodiment exhibits improved solubility in other solvents when a substituent is introduced. Introduction of the substituent also suppresses thermal decomposition of the compound in conducting vacuum deposition.

The substituent may be a substituent that does not decrease the $T_1$ energy of the compound as a whole.

The substituent offers high amorphousness, solubility, and ease of vapor deposition without decreasing $T_1$.

When an alkyl group is introduced as a substituent for the xanthone compound, the alkyl group may have 1 to 4 carbon atoms. This is because a compound having 5 or more carbon atoms renders the compound to be unsuitable for vacuum vapor deposition although the influence on the $T_1$ energy is small.

When an aryl group is introduced as a substituent for the xanthone compound, the aryl group may be selected from benzene, naphthalene, phenanthrene, fluorene, triphenylene, chrysene, pyrene, dibenzofuran, and dibenzothiophene. In particular, the aryl group is preferably selected from benzene, naphthalene, phenanthrene, fluorene, triphenylene, and chrysene.

These aryl groups have a high $T_1$ energy and thus do not decrease the $T_1$ energy of the xanthone compound. The $T_1$ energy of these substituents and references, i.e., anthracene and pyrene, on a wavelength basis are shown in Table 1.

TABLE 1

| | Structural formula | T₁ energy on a wavelength basis |
|---|---|---|
| Benzene | | 339 nm |
| Naphthalene | | 472 nm |
| Phenanthrene | | 459 nm |
| Fluorene | | 422 nm |
| Triphenylene | | 427 nm |
| Chrysene | | 500 nm |
| Dibenzofuran | | 417 nm |
| Dibenzothiophene | | 415 nm |
| Anthracene | | 672 nm |
| Pyrene | | 589 nm |

The xanthone compound may have a substituent introduced into at least one of $R_2$ and $R_7$ among $R_1$ to $R_8$ in general formula [1]. Substituents are preferably introduced into both $R_2$ and $R_7$.

The carbon atoms bonded to $R_2$ and $R_7$ in general formula [1] are susceptible to electrophilic reactions and thus the stability of the molecule as a whole is improved when substituents are introduced to $R_2$ and $R_7$.

The reason that the carbon atoms bonded to $R_2$ and $R_7$ in general formula [1] are susceptible to electrophilic reactions is that these carbon atoms are in para positions with respect to the carbon atoms bonded to the oxygen atoms forming ether bonds in the xanthone skeletons.

A molecular orbital calculation of the B3LYP/6-31G* level was performed on the basis of a density functional theory to determine the $T_1$ energy of the compound 1 set forth in PTL 1 and the compound 2 which is a dimer of xanthone having a carbazolyl group.

The $T_1$ energy of the xanthone compound of this embodiment was also calculated and compared with the results obtained by measuring the phosphorescent spectrum in a diluted toluene solution. Table 2 shows the results.

TABLE 2

| | Structure | T₁ energy on a wavelength basis (calculated) | T₁ energy on a wavelength basis (observed) |
|---|---|---|---|
| Example Compound A-7 | 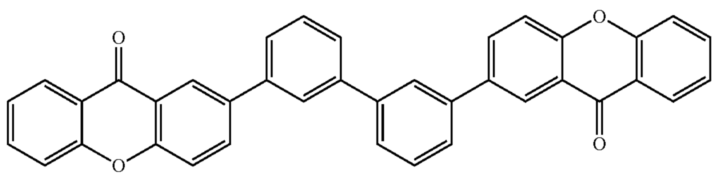 [SMILES: O=c1c2ccccc2oc2ccc(-c3cccc(-c4cccc(-c5ccc6oc7ccccc7c(=O)c6c5)c4)c3)cc12] | 411 nm | 443 nm |
| Example Compound C-1 | 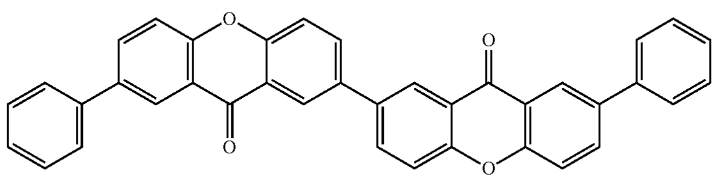 [SMILES: O=c1c2cc(-c3ccccc3)ccc2oc2ccc(-c3ccc4oc5ccc(-c6ccccc6)cc5c(=O)c4c3)cc12] | 427 nm | 446 nm |

TABLE 2-continued

| Structure | $T_1$ energy on a wavelength basis (calculated) | $T_1$ energy on a wavelength basis (observed) |
|---|---|---|
| Compound 1 | 486 nm | — |
| Compound 2 | 470 nm | — |

The difference between the calculated value and the observed value of the $T_1$ energy of two types of xanthone compounds of the present invention was 32 nm and 19 nm.

The difference between the calculated value and the observed value for the compound 1 and the compound 2 can also be estimated to be about 20 to 30 nm on the basis of this result. The estimated observed value is thus about 506 nm to 516 nm. This value is smaller than the $T_1$ energy of the xanthone skeleton itself.

This illustrates that $T_1$ energy of the molecules of these compounds as a whole are small since the carbazolyl groups contained in the compound 1 and the compound 2 affect the $T_1$ energy of the xanthone skeleton.

To investigate the reason therefor, the electron distribution by the molecular orbital calculation was studied. According to the compound 1 and the compound 2, the highest occupied molecular orbital (HOMO) is localized on the N-carbazolyl group and the lowest unoccupied molecular orbital (LUMO) is localized on the xanthone skeleton.

As a result, the compound 1 and the compound 2 enter an electron transfer (CT) excitation state, and thus the excited singlet ($S_1$) and $T_1$ energy decreases significantly.

This shows that in order to keep the high $T_1$ energy of the xanthone skeleton, introduction of a substituent, such as a carbazolyl group, having a high HOMO level energy is to be avoided.

Introduction of an electron-donating substituent, such as a N-carbazolyl group or an amino group, is also not favorable from the viewpoint of a decrease in electron accepting property of the xanthone skeleton.

The xanthone compound of this embodiment has a linking group L. The linking group L as well as the substituents has an influence on the $T_1$ energy of the molecule as a whole.

Accordingly, L in general formula [1] may be benzene, naphthalene, phenanthrene, fluorene, triphenylene, chrysene, dibenzofuran, dibenzothiophene, biphenyl, or terphenyl.

In addition to the substituents named as examples of the aryl group used as the substituent, biphenyl or terphenyl can be used as the linking group. This is because $T_1$ of biphenyl is 445 nm, $T_1$ of o-terphenyl is 464 nm, $T_1$ of m-terphenyl is 445 nm, and $T_1$ of p-terphenyl is 491 nm, which are sufficiently high.

L in general formula [1] may have an alkyl group having 1 to 4 carbon atoms as a substituent. When L has an alkyl group as a substituent, the thermal stability and amorphousness of the molecule as a whole are improved.

L in general formula [1] may be free of a substituent, such as an aryl group, that affects the $T_1$ energy.

The stability of the compound can be improved depending on the positions to which L is linked in general formula [1].

Specifically, L in general formula [1] may be linked to positions shown in general formula [2] below.

[Chem. 5]

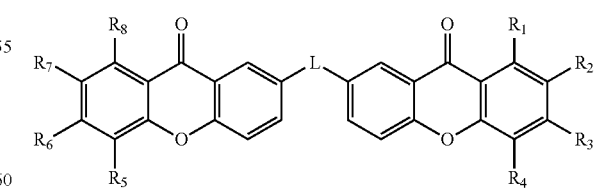

[2]

$R_1$ to $R_8$ and L in general formula [2] are the same as those of general formula [1]. In order to improve the stability in the compound, substituents may be introduced to $R_2$ and $R_7$. Accordingly, a xanthone compound represented by general formula [3] is particularly favorable.

[Chem. 6]

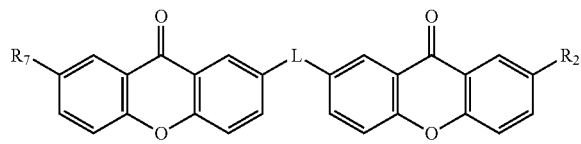

[3]

$R_2$ and $R_7$ in general formula [3] are the same as those in general formula [1] except that they are not hydrogen atoms. L in general formula [3] is the same as that in general formula [1].

The xanthone compound has high $T_1$ and electron mobility and may thus be used in an organic compound layer of an organic light-emitting device.

In particular, the xanthone compound may be used as a host material of an emission layer or as a material for a layer adjacent to a cathode-side of the emission layer.

A host material is a material having the largest weight ratio among the materials constituting the emission layer. A guest material is a material having a weight ratio smaller than the host material and is accountable for main emission among the materials constituting the emission layer. An assisting material is a material having a weight ratio smaller than that of the host material and assists emission of the guest material among the materials constituting the emission layer. An assisting material is also referred to as a host material 2.

The xanthone compound can be used as a host material of an emission layer of a blue or green phosphorescence-emitting device.

Here, blue means that the emission wavelength is in the range of 440 nm or more and 480 nm or less and green means that the emission wavelength is in the range of 500 nm or more and 530 nm or less.

Since the xanthone compound has high electron mobility, the xanthone compound can be used in an electron transport layer or an electron injection layer of a blue or green phosphorescence-emitting device.

The electron transport layer is a layer that is adjacent to the emission layer and transports electrons among the organic compound layers of an organic light-emitting device. It can also be referred to as a layer that is adjacent to a cathode side of the emission layer among the organic compound layers of the organic light-emitting device.

This layer may have a $T_1$ energy higher than that of the emission material to prevent migration of the energy from the emission layer to the adjacent layer.

The electron injection layer is a layer that receives electrons from an electrode and transfers the electrons to the electron transport layer.

The electron injection layer can also be referred to as a layer in contact with a cathode and disposed between the electron transport layer and the cathode.

This layer may have high electron injectability and thus a compound having a deep LUMO level may be used in this layer.

The phrase, "deep LUMO or HOMO level" means that the concerned level is distant from a vacuum level. That the LUMO level is shallow means that the level is close to the vacuum level.

Since the xanthone compound of the present invention has a low LUMO level, the xanthone compound can be used as an electron injection material, an electron transport material, or a host material of a hole blocking layer or an emission layer and can thereby decrease the driving voltage of the device.

This is because the electron injection barrier from the hole blocking layer or the electron transport layer adjacent to the cathode-side of the emission layer is lowered when the LUMO level is low.

Specific examples of structural formulae of the xanthone compound of the present invention are given below. The present invention is not limited to these example compounds.

[Chem. 7]

A-1

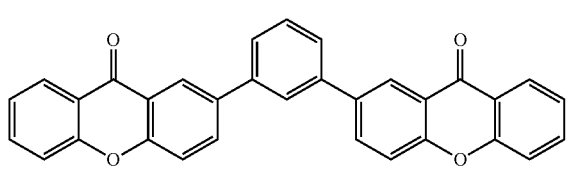

A-2

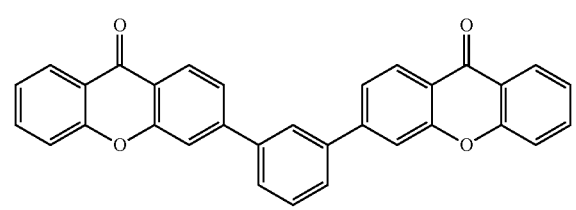

A-3

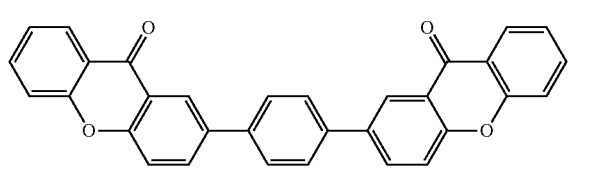

A-4

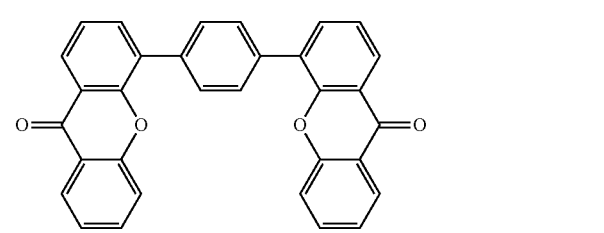

-continued
A-5
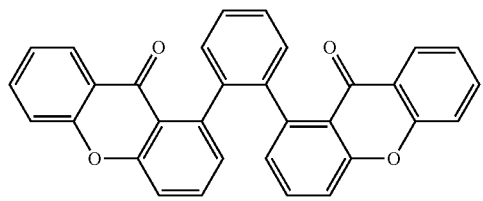
A-6
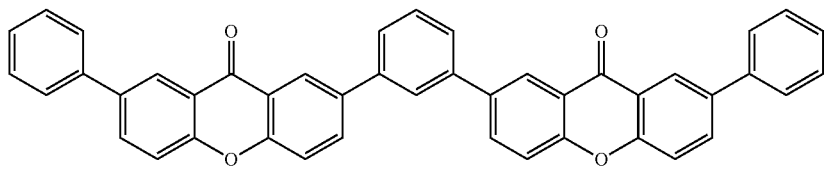
A-7
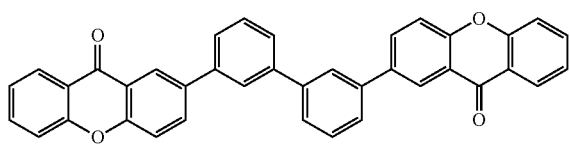
A-8
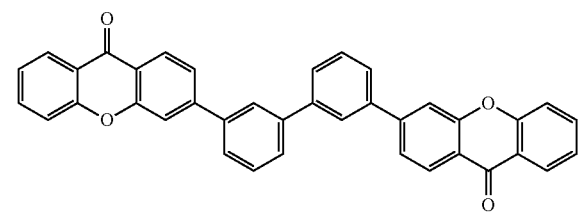
A-9
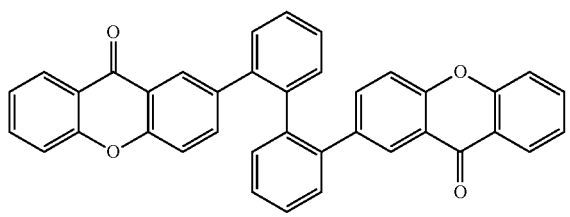
A-10
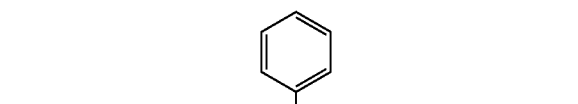
A-11
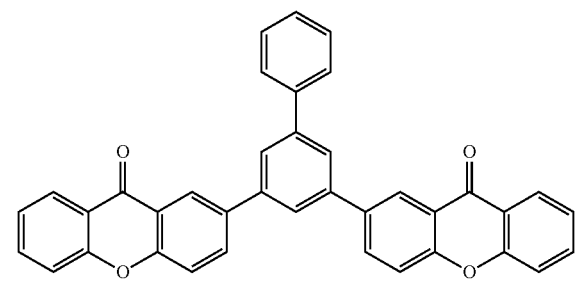
A-12
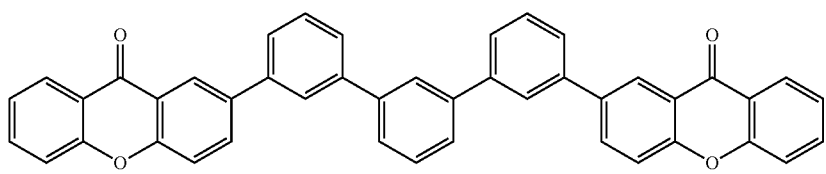
A-13
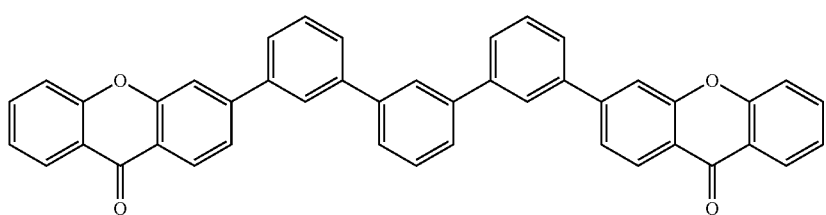
A-14
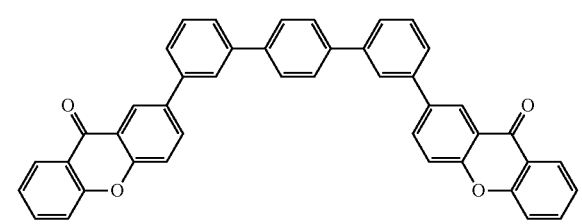

-continued
[Chem. 8]
A-15
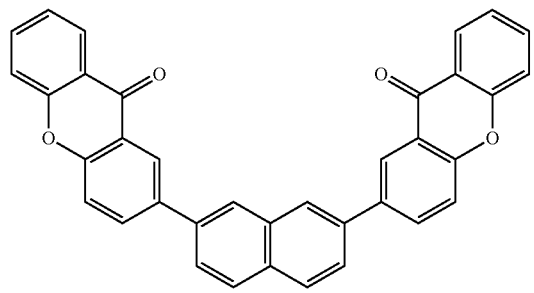
A-16
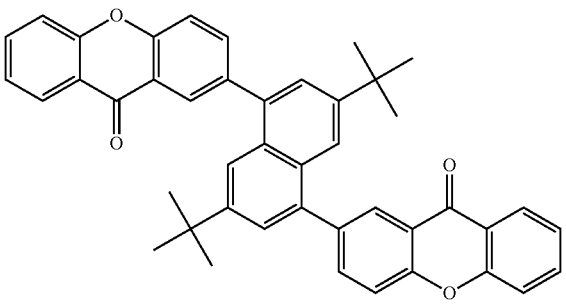
A-17
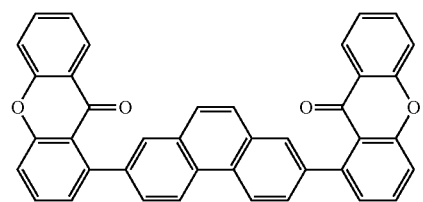
A-18
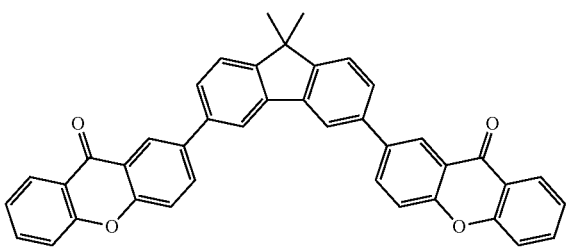
A-19
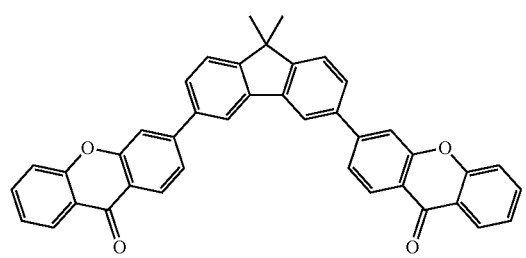
A-20
A-21
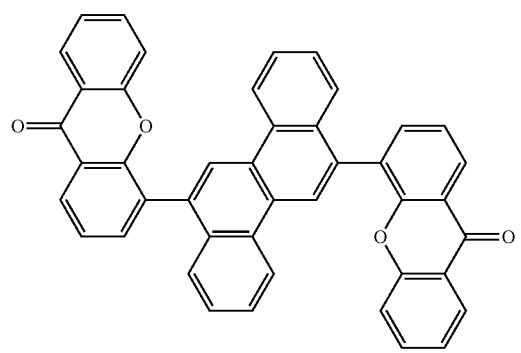
A-22
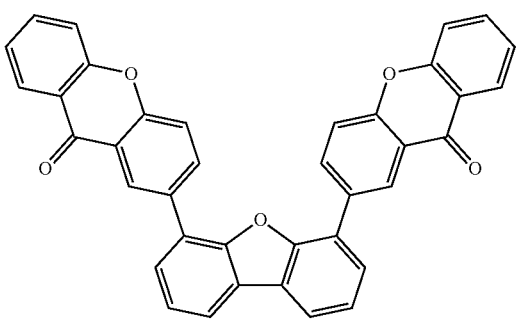
A-23
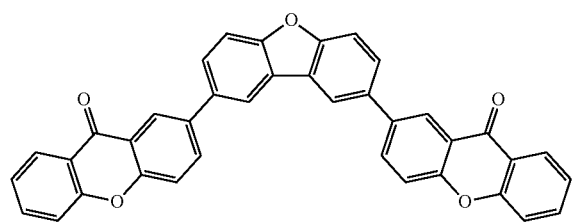
A-24
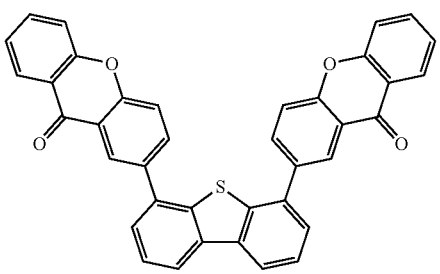

-continued
A-25
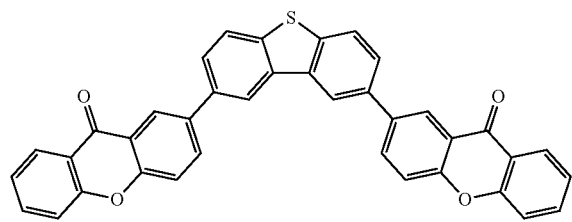
A-26
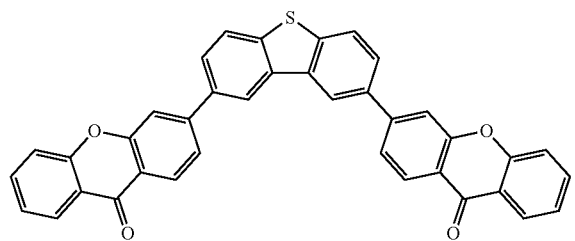
[Chem. 9]
B-1
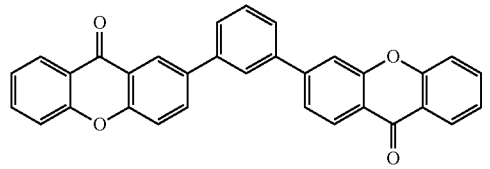
B-2
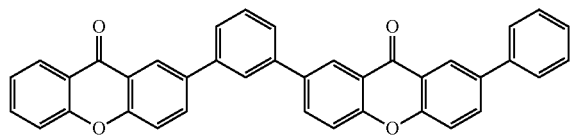
B-3
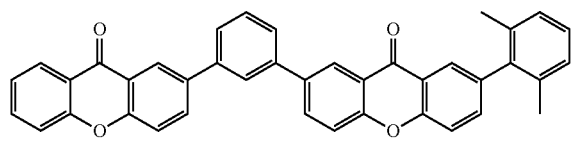
B-4
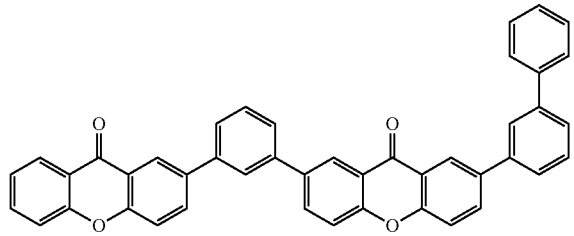
B-5
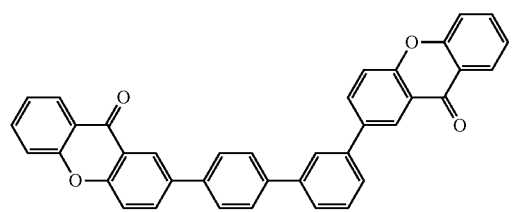
B-6
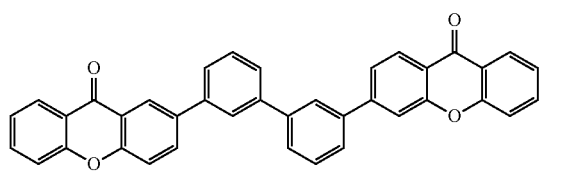
B-7
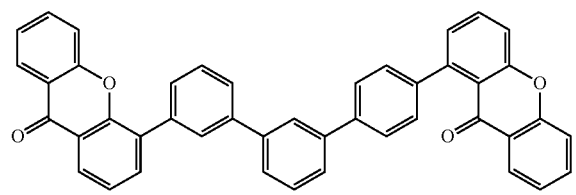
B-8
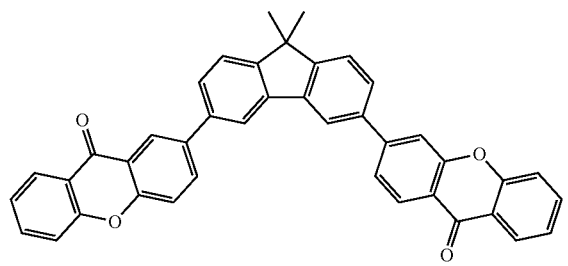
B-9
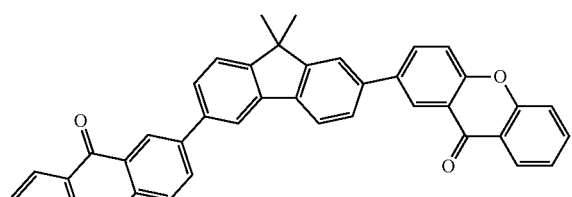
B-10
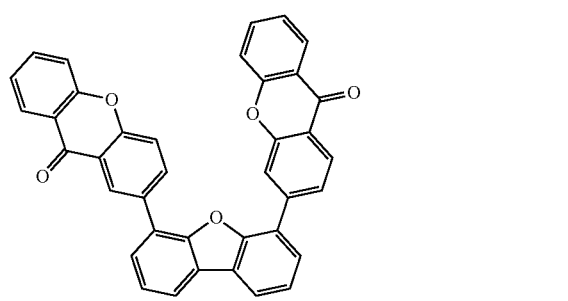

-continued
B-11
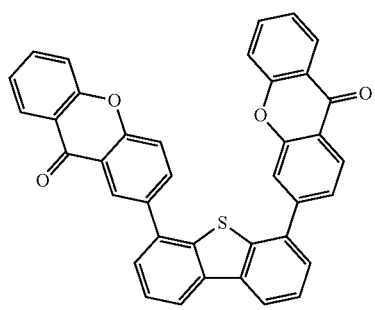
B-12
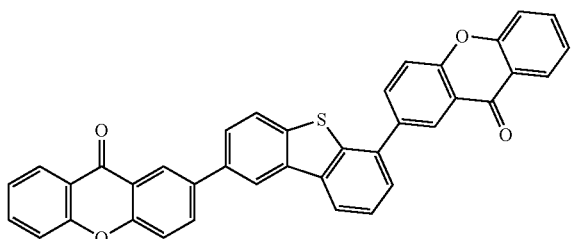
[Chem. 10]
C-1
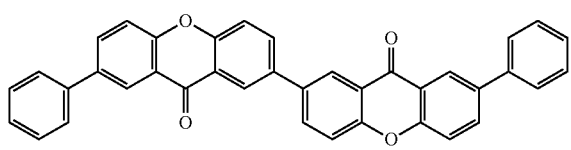
C-2
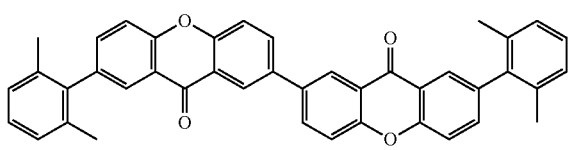
C-3
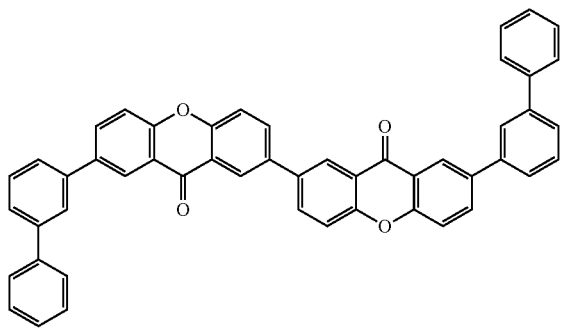
C-4
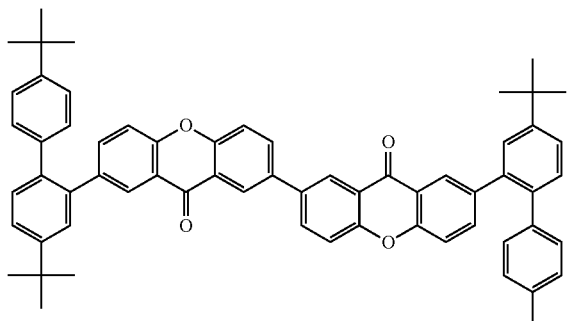
C-5
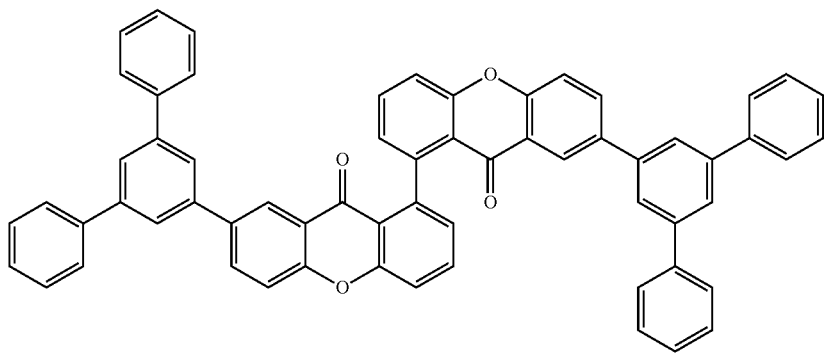
C-6
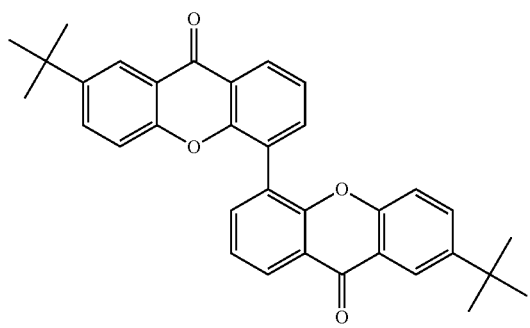

-continued
[Chem. 11]
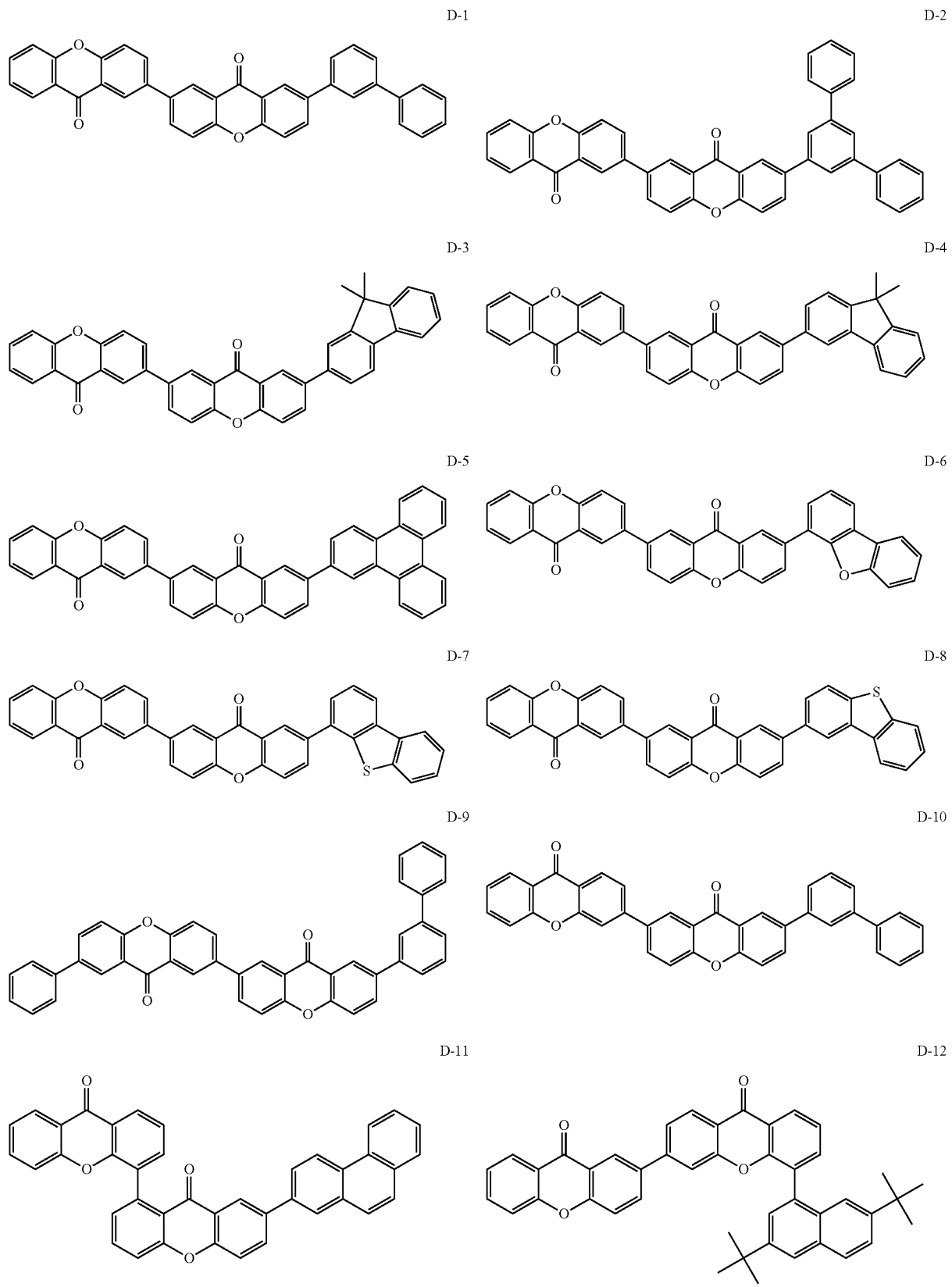

Properties of Example Compounds

Example Compounds of Group A have L representing an aromatic ring substituent and have a plane or axis of symmetry within a molecule. The two xanthone skeletons have a similar electronic state, are free of bias in electronic distribution, and are thus stable.

Example Compounds of Group B have L representing an aromatic ring substituent and have no plane or axis of symmetry within a molecule. Accordingly, higher stability is achieved in an amorphous state. Moreover, the physical property values can be finely adjusted by varying the position and type of the substituent.

Example Compounds of Group C have L representing a single bond and have a plane or axis of symmetry within a molecule. The electronic distribution is not biased and thus the compounds are stable. Since the two xanthone skeletons are directly bonded to each other, the electron accepting property is further enhanced, which effectively contributes to voltage reduction of an organic light-emitting device.

Example Compounds of Group D have L representing a single bond and have no plane or axis of symmetry within a molecule. Accordingly, these compounds are effective for decreasing voltage and improving the amorphousness. The physical property values can be finely adjusted by varying the position and type of the substituent.

Description of Synthetic Route

One example of a synthetic route for an organic compound of the present invention will now be described. The reaction scheme is as follows.

Xanthone and its derivatives are widely commercially available. A halide, triflate, or boronic acid ester thereof can be easily synthesized from a commercially available product.

[Chem. 12]

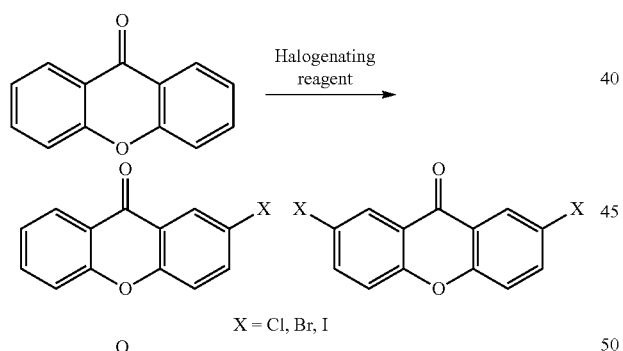

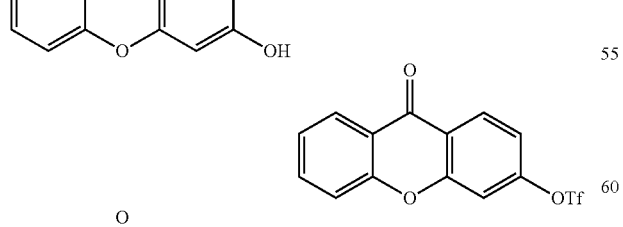

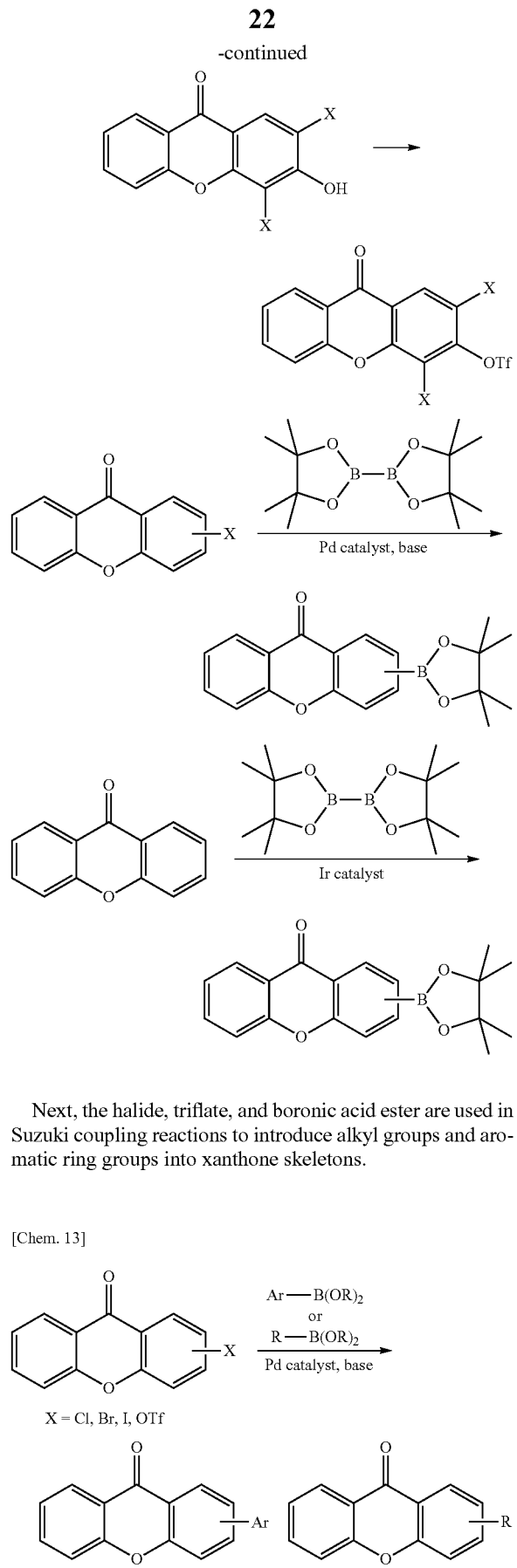

Next, the halide, triflate, and boronic acid ester are used in Suzuki coupling reactions to introduce alkyl groups and aromatic ring groups into xanthone skeletons.

[Chem. 13]

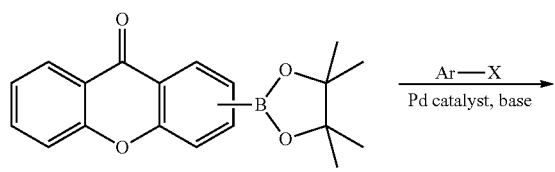

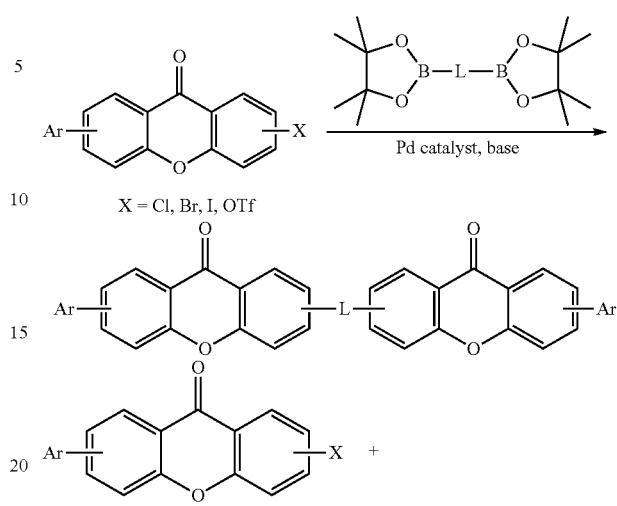

Alternatively, a Friedel-Crafts reaction may be employed to introduce alkyl groups into xanthone skeletons.

[Chem. 14]

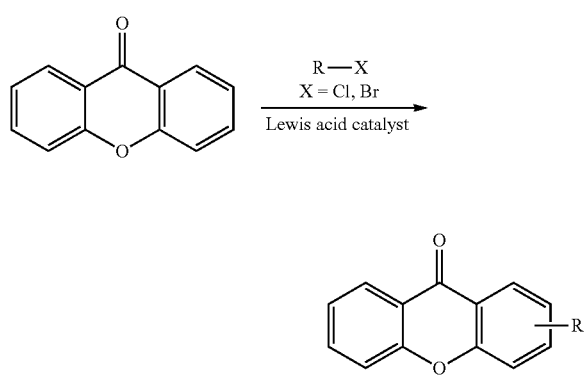

Yet alternatively, a dihydroxybenzophenone derivative already having a reactive functional group or an aromatic ring group may be used to conduct a dehydration condensation reaction so that the xanthone skeletons are constructed later.

[Chem. 15]

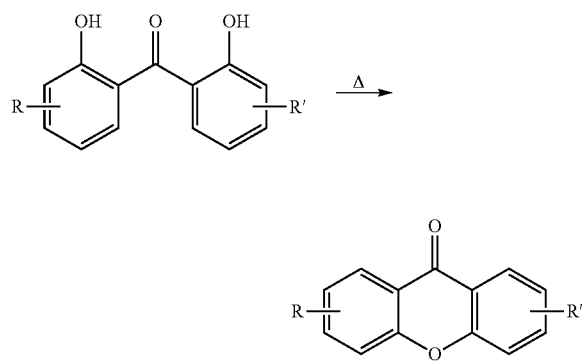

The basic reactions described above are combined with one another in a variety of ways to synthesize a xanthone compound having desired substituents introduced into desired positions among $R_1$ to $R_8$ in general formula [1].

Properties of Organic Light-Emitting Device According to an Embodiment

An organic light-emitting device according to an embodiment of the present invention includes an anode and a cathode which are a pair of electrodes, and organic compound layers disposed between the anode and the cathode. Of the organic compound layers, a layer that contains a phosphorescent material is an emission layer.

According to the organic light-emitting device of this embodiment, a xanthone compound represented by general formula [1] is contained in an organic compound layer.

The organic light-emitting device of this embodiment may include one or more organic compound layers.

When only one organic compound layer is included, the organic layer is an emission layer.

When two or more organic compound layers are included, these layers are selected from a hole injection layer, a hole transport layer, an emission layer, a hole blocking layer, an electron transport layer, an electron injection layer, an exciton blocking layer, etc. Two or more of the layers may be selected from these layers and used in combination.

The configuration of the organic light-emitting device according to this embodiment is not limited to these. For example, various other layer configurations may be employed, e.g., an insulating layer may be provided at the interface between an electrode and an organic compound layer, an adhesive layer or an interference layer may be provided, and the electron transport layer or the hole transport layer may be constituted by two layers having different ionization potentials.

The device may be of a top emission type that emits light from the substrate-side electrode or of a bottom emission type that emits light from the side opposite the substrate. The device may be of a type that emits light from both sides.

The organic light-emitting device according to this embodiment may contain a xanthone compound represented by general formula [1] as a material for an electron transport layer or a host material of an emission layer.

When the xanthone compound is used in the electron transport layer, the xanthone compound may be used alone or in combination with another compound.

The concentration of the host material in the emission layer is 50 wt % or more and 99.9 wt % or less and preferably 80 wt % or more and 99.9 wt % or less relative to the total weight of the emission layer. In order to prevent concentration quenching, the concentration of the guest material is preferably 0.01 wt % or more and 10 wt % or less.

The guest material may be homogeneously distributed in the entire layer composed of a host material, may be contained in the layer by having a concentration gradient, or may be contained in particular parts of the layer, thereby creating parts only the host material is contained.

In the organic light-emitting device of this embodiment, the xanthone compound represented by general formula [1] may be contained as an assisting material of the emission layer. The host material of the emission layer in such a case may be a compound having high hole transport property.

This is because the xanthone compound of the present invention is a compound having high electron transport property.

When a compound having high hole transport property and a compound having high electron transport property are used in combination, the emission layer achieves bipolar emission.

The transport properties of the two compounds combined can adjust the carrier balance in the emission layer.

Note that the hole transport property and electron transport property are "high" when the mobility is $10^{-4}$ cm$^2$/(V·s) or more. This value can be measured by a time-of-flight (TOF) technique.

The color of emission of the phosphorescent material is not particularly limited but may be blue to green with a maximum emission peak wavelength within a range of 440 nm or more and 530 nm or less.

In order to prevent a decrease in emission efficiency caused by radiationless deactivation from $T_1$ of the host material of the phosphorescence-emitting device, the $T_1$ energy of the host material may be higher than the $T_1$ energy of the phosphorescent material which is a guest material.

Since the $T_1$ energy of the xanthone skeleton that functions as the center of the xanthone compound is 410 nm, the $T_1$ energy of the xanthone compound is higher than the $T_1$ energy of a blue phosphorescent material.

Accordingly, when the xanthone compound is used in an emission layer or a nearby layer of a blue to green phosphorescence-emitting device, high emission efficiency can be achieved.

When the xanthone compound is used as an electron transport material, an assisting material, or a host material in a phosphorescent layer, a phosphorescent material used as a guest material is a metal complex such as an iridium complex, a platinum complex, a rhenium complex, a copper complex, an europium complex, or a ruthenium complex. Among these, an iridium complex having a high phosphorescent property is preferred. Two or more phosphorescent materials may be contained in the emission layer to assist transmission of excitons and carriers.

Examples of the iridium complex used as the phosphorescent material and examples of the host material are presented below. These examples do not limit the scope of the present invention.

[Chem. 17]

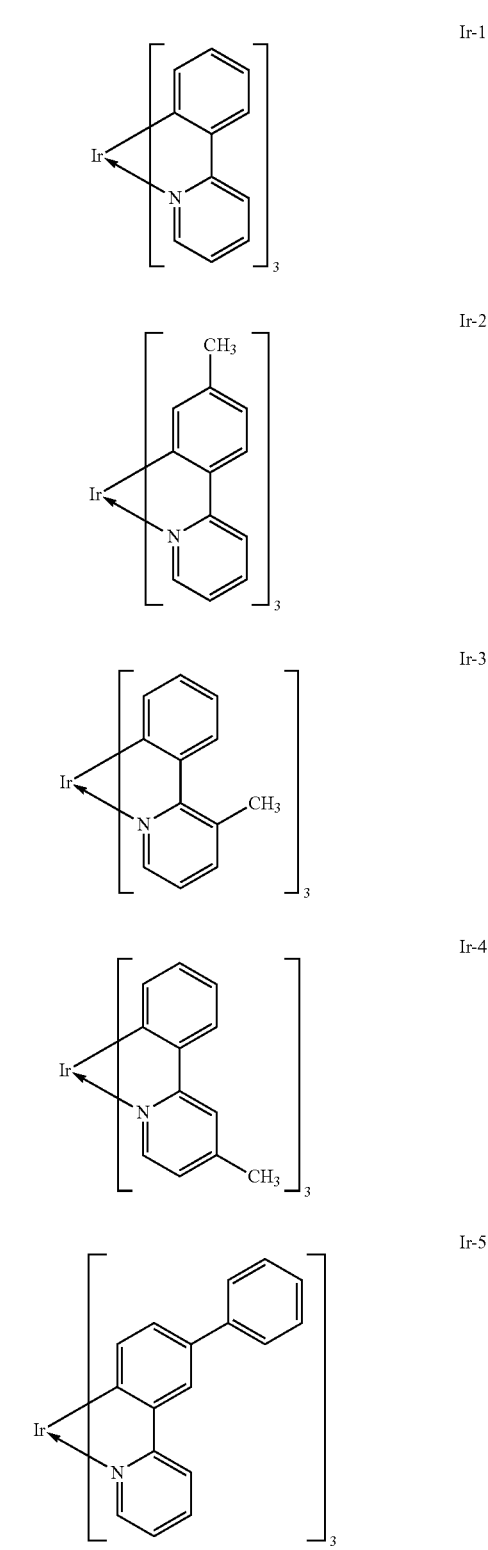

-continued
Ir-6
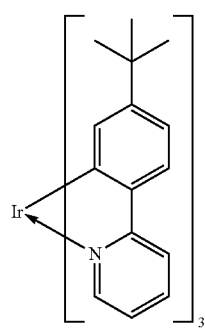
Ir-7
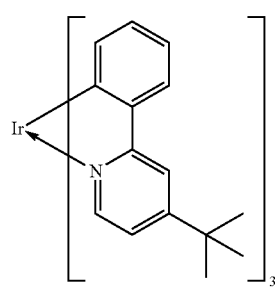
Ir-8
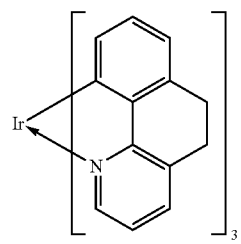
Ir-9
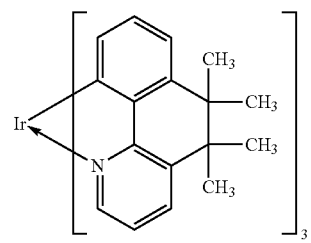
Ir-10
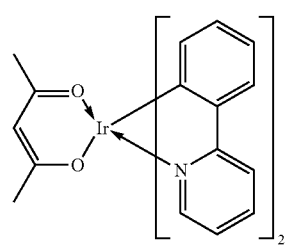
-continued
Ir-11
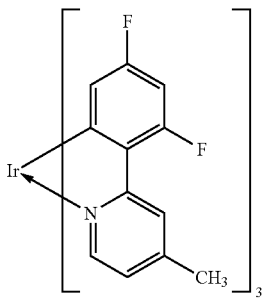
Ir-12
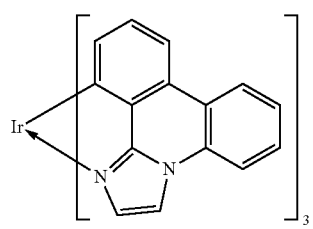
Ir-13
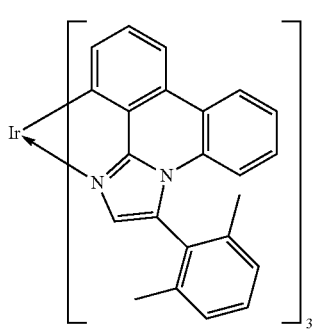
Ir-14
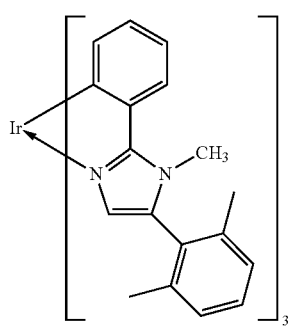
Ir-15
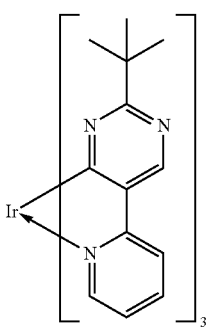

Ir-16
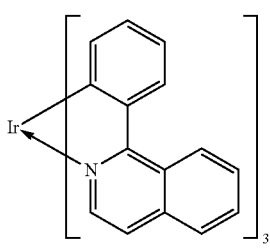
Ir-17
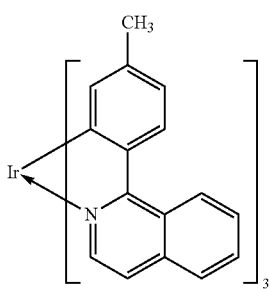
Ir-18
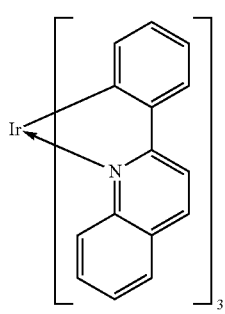
Ir-19
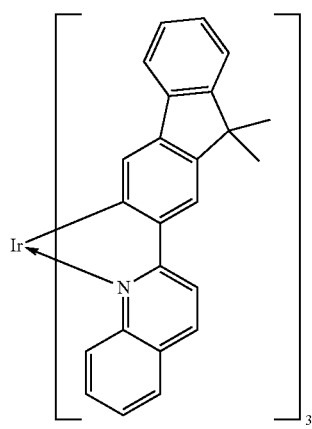
Ir-20
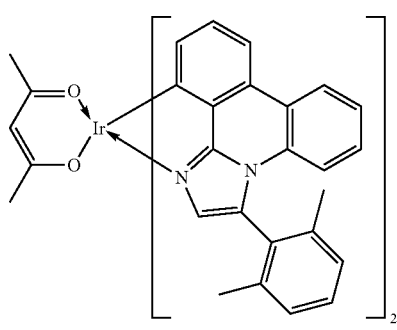
Ir-21
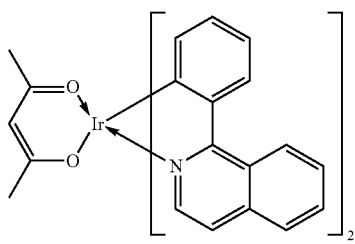
Ir-22
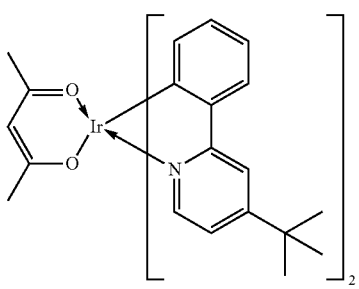
Ir-23
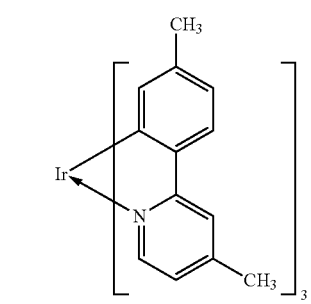
Ir-24
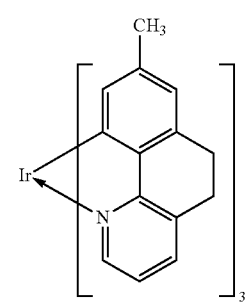
Ir-25
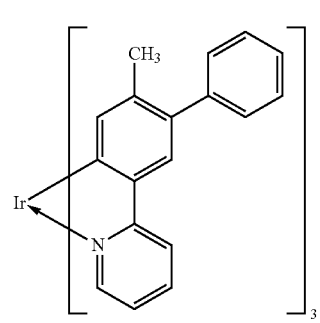

-continued
Ir-26
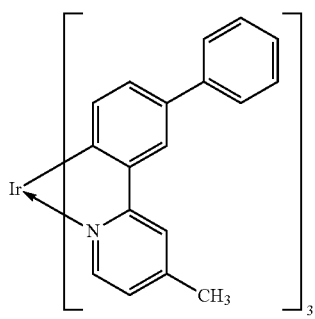
Ir-27
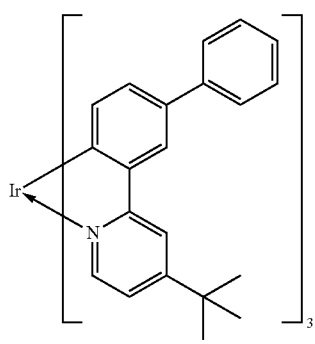
[Chem. 18]
I-1
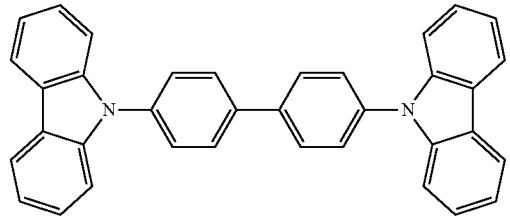
I-2
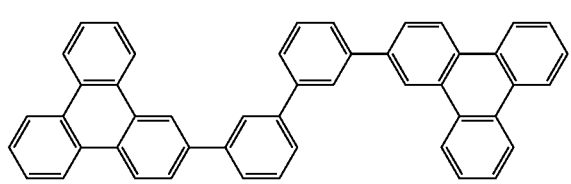
I-3
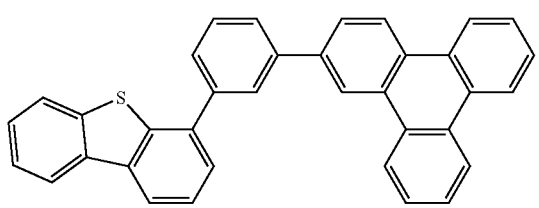
I-4
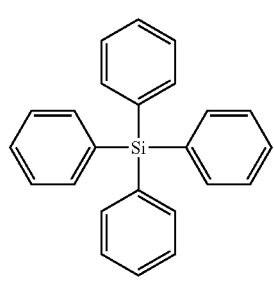
-continued
I-5
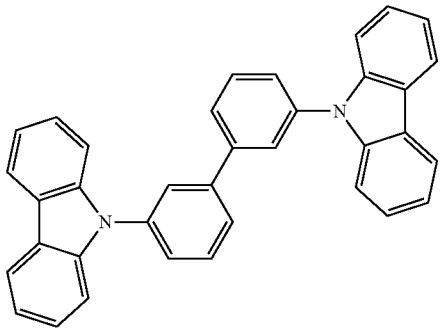
I-6
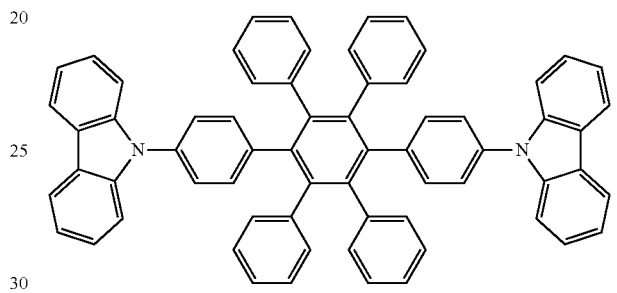
I-7
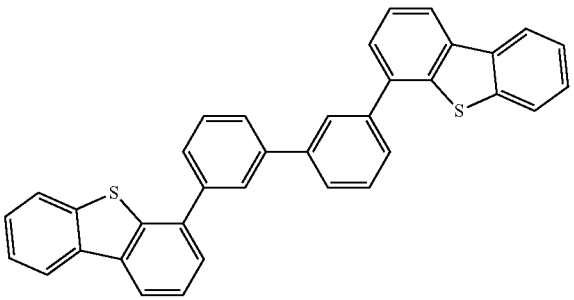
I-8
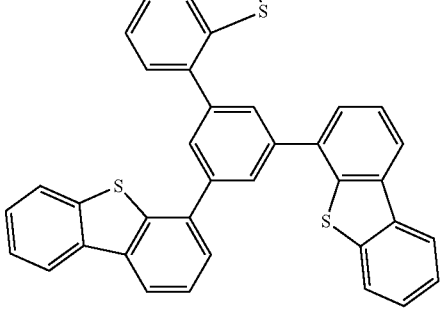

-continued

I-9

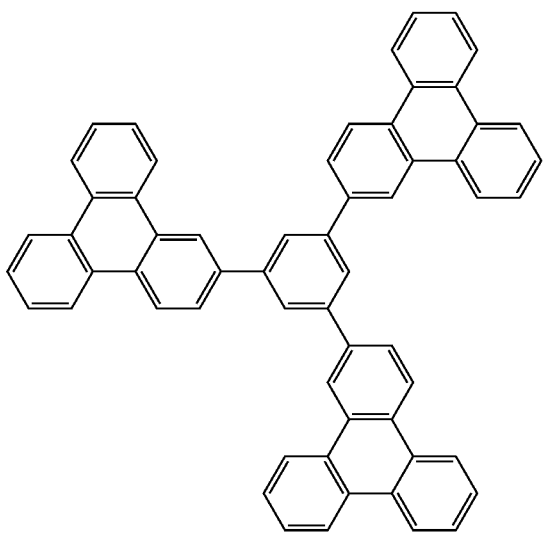

If needed, a common low-molecular-weight or high-molecular-weight compound may be used in addition to the xanthone compound. For example, a hole injection or transport compound, a host material, a light-emitting compound, or an electron injection or transport compound may be used in combination.

Examples of these compounds are presented below.

The hole injection/transport material can be a material having a high hole mobility so that holes can be easily injected from the anode and the injected holes can be easily transported to the emission layer. Examples of the low- and high-molecular-weight materials having hole injection/transport property include triarylamine derivatives, phenylenediamine derivatives, stilbene derivatives, phthalocyanine derivatives, porphyrin derivatives, poly(vinyl carbazole), poly(thiophene), and other conductive polymers.

Examples of the light-emitting material mainly contributing to the light-emitting function include the phosphorescent guest materials described above, derivative thereof, fused compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolato) aluminum, organic beryllium complexes, and polymer derivatives such as poly(phenylenevinylene) derivatives, poly (fluorene) derivatives, and poly(phenylene) derivatives.

The electron injection/transport material may be selected from materials to which electrons can be easily injected from the cathode and which can transport the injected electrons to the emission layer. The selection may be made by considering the balance with the hole mobility of the hole injection/transport material. Examples of the electron injection/transport material include oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The anode material may have a large work function. Examples of the anode material include single metals such as gold, platinum, silver, copper, nickel, palladium, cobalt, selenium, vanadium, and tungsten or alloys thereof, and metal oxides such as tin oxide, zinc oxide, indium oxide, indium tin oxide (ITO), and indium zinc oxide. Conductive polymers such as polyaniline, polypyrrole, and polythiophene may also be used. These anode materials may be used alone or in combination. The anode may be constituted by one layer or two or more layers.

The cathode material may have a small work function. Examples of the cathode material include alkali metals such as lithium, alkaline earth metals such as calcium, and single metals such as aluminum, titanium, manganese, silver, lead, and chromium. The single metals may be combined and used as alloys. For example, magnesium-silver, aluminum-lithium, and aluminum-magnesium alloys and the like can be used. Metal oxides such as indium tin oxide (ITO) can also be used. These cathode materials may be used alone or in combination. The cathode may be constituted by one layer or two or more layers.

Layers containing the xanthone compound and other organic compounds in the organic light-emitting device are formed by the following processes. Typically, thin films are formed by vacuum vapor deposition, ionization deposition, sputtering, plasma, and coating using an adequate solvent (spin-coating, dipping, casting, a Langmuir Blodgett method, and an ink jet method). When layers are formed by vacuum vapor deposition or a solution coating method, crystallization is suppressed and stability over time can be improved. When a coating method is employed, an adequate binder resin may be additionally used to form a film.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or in combination of two or more as a copolymer. If needed, known additives such as a plasticizer, an antioxidant, and an ultraviolet absorber may be used in combination.

Usage of Organic Light-Emitting Device

The organic light-emitting device of the embodiment may be used in a display apparatus or a lighting apparatus. The organic light-emitting device can also be used as exposure light sources of electrophotographic image-forming apparatuses and backlights of liquid crystal display apparatuses.

A display apparatus includes a display unit that includes the organic light-emitting device of this embodiment. The display unit has pixels. Each pixel has the organic light-emitting device of this embodiment and a thin film transistor (TFT) element, which is an example of a switching element for controlling emission luminance. The drain electrode or source electrode of the TFT element is coupled to the anode or cathode of the organic light-emitting device. The display apparatus can be used as an image display apparatus of a personal computer, etc.

The display apparatus may be an image input device that has an input unit through which image data is input from an area CCD, a linear CCD, a memory card, or the like and the input image is output in a display unit. The display apparatus may function as a display unit of an imaging apparatus or an ink jet printer and may have both an image output function of displaying image data input from outside and an input function of an operation panel through which image processing data is input. The display apparatus may be used as a display unit of a multifunction printer.

Next, a display apparatus that uses the organic light-emitting device according to the embodiment is described with reference to FIG. 1.

FIG. 1 is a schematic cross-sectional view of a display apparatus that includes organic light-emitting devices of this embodiment and TFT elements, which is one example of a switching element coupled to the organic light-emitting device. In the drawing, two pairs of the organic light-emitting device and the TFT element are illustrated. The detailed structure is as follows.

The display includes a substrate 1 such as glass and a moisture proof film 2 for protecting the TFT elements and the organic compound layers, the moisture proof film 2 being disposed on the substrate 1. The display also includes a metal gate electrode 3, a gate insulating film 4, and a semiconductor layer 5.

A TFT element 8 includes the semiconductor layer 5, a drain electrode 6, and a source electrode 7. An insulating film 9 is disposed over the TFT element 8. An anode 11 of the organic light emitting device is coupled to the source electrode 7 through a contact hole 10. The configuration of the display apparatus is not limited to this as long as one of the anode and the cathode is coupled to one of the source electrode and the drain electrode of the TFT element.

In the drawing, an organic compound layer 12 is illustrated as one layer but is constituted by a plurality of layers. A first protective layer 14 and a second protective layer 15 for suppressing deterioration of the organic light-emitting device are provided over the cathode 13.

In the display apparatus of this embodiment, the switching element is not particularly limited. For example, a single crystal silicon substrate, a metal-insulator-metal (MIM) element, or an a-Si element may be used.

EXAMPLES

Examples will now be described. The present invention is not limited to these examples.

Example 1

Synthesis of Example Compound A-7

[Chem. 19]

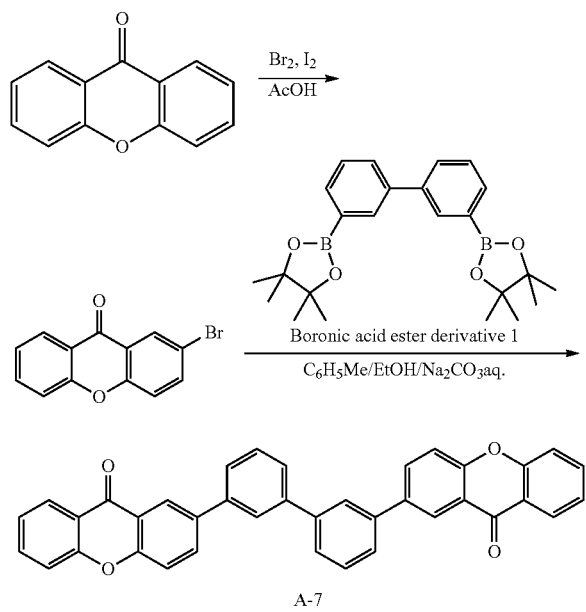

A-7

To a 100 mL round-bottomed flask, the following reagents and solvents were placed.

Xanthone: 5.0 g (26 mmol)

Bromine: 16 g (102 mmol)

Iodine: 50 mg (0.20 mmol)

Acetic acid: 20 mL

The resulting reaction solution was refluxed for 5 hours at 100° C. under heating and stirring in nitrogen. Upon completion of the reaction, chloroform and a saturated aqueous sodium sulfite solution were added to the reaction solution and stirring was continued until the color of bromine was lost. The organic layer was separated, washed with a saturated aqueous sodium carbonate solution, dried with magnesium sulfate, and filtered. The solvent in the filtrate was distilled away at a reduced pressure. The precipitated solid was purified with a silica gel column (toluene: 100%). As a result, 2.9 g (yield: 41%) of 2-bromoxanthone and 2.2 g (yield: 25%) of 2,7-dibromoxanthone were obtained.

The following reagents and solvents were placed in a 50 mL round-bottomed flask.

2-Bromoxanthone: 1.5 g (5.4 mmol)

Boronic acid ester derivative 1: 1.0 g (2.5 mmol)

Tetrakis(triphenylphosphine)palladium(0): 0.29 g (0.25 mmol)

Toluene: 10 mL

Ethanol: 2 mL

2M Aqueous sodium carbonate solution: 6 mL

The reaction solution was refluxed for 12 hours under heating and stirring in nitrogen. Upon completion of the reaction, the precipitated solid was filtered and washed with water, methanol, and acetone. The resulting solid was dissolved in chlorobenzene under heating and insolubles were removed by hot-filtering the solution. The solvent in the filtrate was distilled away at a reduced pressure and the precipitated solid was recrystallized in a chlorobenzene/heptane system. The resulting crystals were vacuum dried at 150° C. and purified by sublimation at $10^{-1}$ Pa and 370° C. As a result, 0.44 g (yield: 33%) of Example Compound A-7 having high purity was obtained.

$M^+$ of this compound, i.e., 542.2, was confirmed by matrix-assisted laser desorption ionization-time-of-flight mass spectroscopy (MALDI-TOF-MS).

The structure of the compound was confirmed by proton nuclear magnetic resonance spectroscopy ($^1$H-NMR).

$^1$H-NMR (CDCl$_3$, 500 MHz) δ (ppm): 8.65 (2H, d), 8.39 (2H, dd), 8.08 (2H, dd), 7.96 (2H, bs), 7.78-7.74 (2H, m), 7.74-7.69 (4H, m), 7.65-7.58 (4H, m), 7.55 (2H, d), 7.44-7.39 (2H, m)

The T$_1$ energy of Example Compound A-7 was measured by the following method.

A phosphorescence spectrum of a diluted toluene solution (1×10$^{-5}$ M) of Example Compound A-7 was measured in an Ar atmosphere at 77 K and an excitation wavelength of 350 nm. The T$_1$ energy was calculated from the peak wavelength of the 0-0 band (first emission peak) of the obtained phosphorescence spectrum. The T$_1$ energy was 443 nm on a wavelength basis.

Example 2
Synthesis of Example Compound A-1
[Chem. 20]
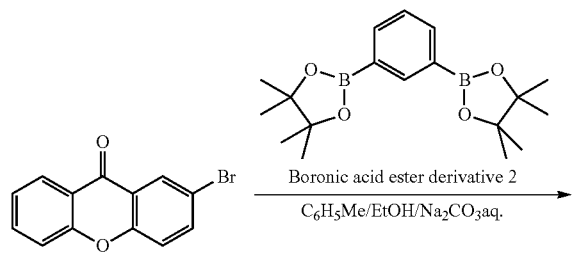
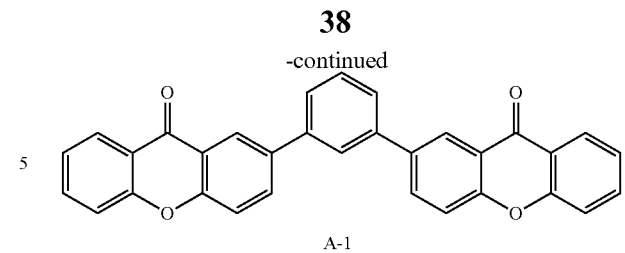
A-1
Example Compound A-1 was obtained as in Example 1 except that the boronic acid ester derivative 1 used in Example 1 was changed to a boronic acid ester derivative 2.
$M^+$ of this compound, 466.1, was confirmed by MALDI-TOF MS.
Example 3
Synthesis of Example Compound A-6
[Chem. 21]
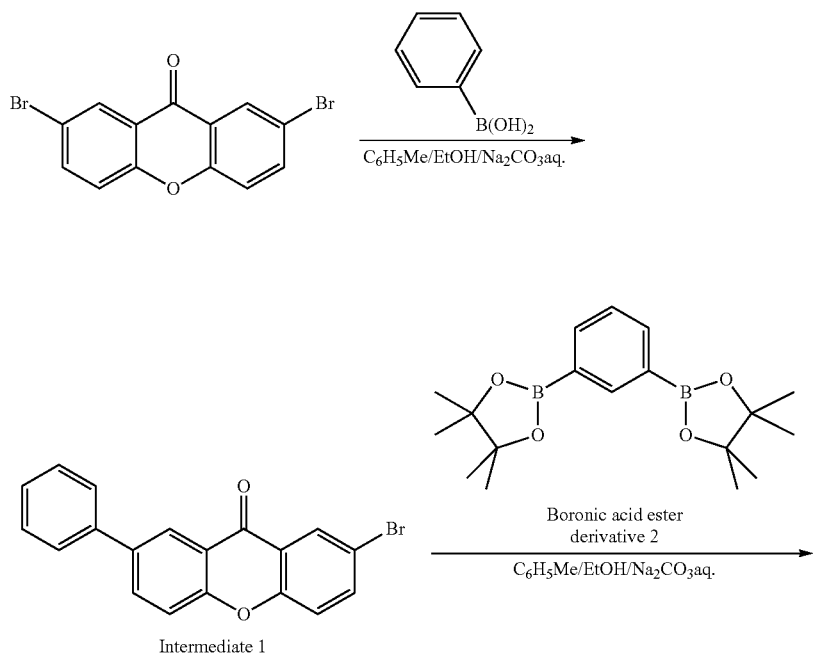
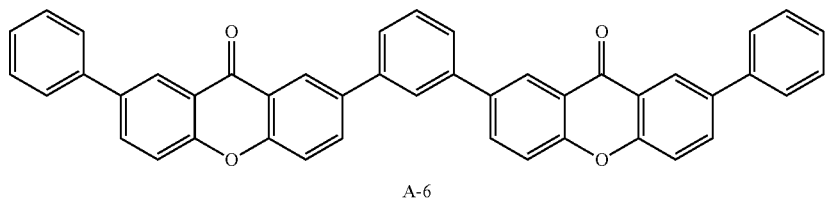
A-6

The following reagents and solvents were placed in a 100 mL round-bottomed flask.
2,7-Dibromoxanthone: 3.1 g (8.6 mmol)
Phenylboronic acid: 1.1 g (8.6 mmol)
Tetrakis(triphenylphosphine)palladium(0): 0.50 g (0.43 mmol)
Toluene: 20 mL
Ethanol: 2 mL
2M Aqueous sodium carbonate solution: 10 mL The reaction solution was refluxed for 10 hours under stirring and heating in nitrogen. Upon completion of the reaction, the organic layer was separated, dried with magnesium sulfate, and filtered. The solvent in the obtained filtrate was distilled away at a reduced pressure. The precipitated solid was purified with a silica gel column (chloroform:heptane=1:1). As a result, 1.24 g (yield: 41%) of intermediate 1 was obtained.

Example Compound A-6 was synthesized as in Example 2 except that 2-bromoxanthone used in Example 2 was changed to intermediate 1.

M+ of this compound, 618.2, was confirmed by MALDI-TOF MS.

Example 4

Synthesis of Example Compound C-1

[Chem. 22]

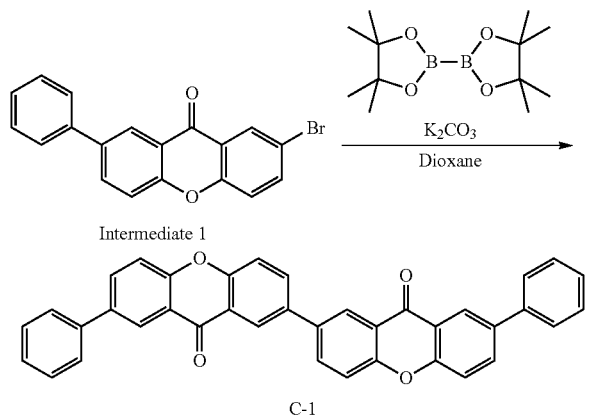

The following reagents and solvents were placed in a 100 mL round-bottomed flask.
Intermediate 1: 1.0 g (2.9 mmol)
Bis(pinacolato)diboron: 0.45 g (1.8 mmol)
Potassium carbonate: 2.0 g (15 mmol)
Bis(triphenylphosphine)palladium(II) dichloride: 0.20 g (0.29 mmol)
Dioxane: 15 mL The reaction solution was refluxed for 12 hours under heating and stirring in nitrogen. Upon completion of the reaction, precipitated solid was filtered and washed with water, methanol, and acetone. The obtained solid was dissolved in chlorobenzene under heating and insolubles were removed by hot-filtering the solution. The solvent in the filtrate was distilled away at a reduced pressure and the precipitated solid was recrystallized with a chlorobenzene/heptane system. The resulting crystals were vacuum dried at 150° C. and purified by sublimation at 10$^{-1}$ Pa and 380° C. As a result, 0.45 g (yield: 57%) of Example Compound C-1 having high purity was obtained.

M+ of this compound, 542.2, was confirmed by MALDI-TOF MS.

The structure of the compound was confirmed by $^1$H-NMR.

$^1$H-NMR (CDCl$_3$, 500 MHz) δ (ppm): 8.69 (2H, d), 8.62 (2H, d), 8.14 (2H, dd), 8.02 (2H, dd), 7.74-7.70 (4H, m), 7.68 (2H, d), 7.64 (2H, d), 7.53-7.48 (4H, m), 7.43-7.39 (2H, m)

The T$_1$ energy of Example Compound C-1 was measured as in Example 1. The T$_1$ energy was 446 nm on a wavelength basis.

Example 5

Synthesis of Example Compound D-1

[Chem. 23]

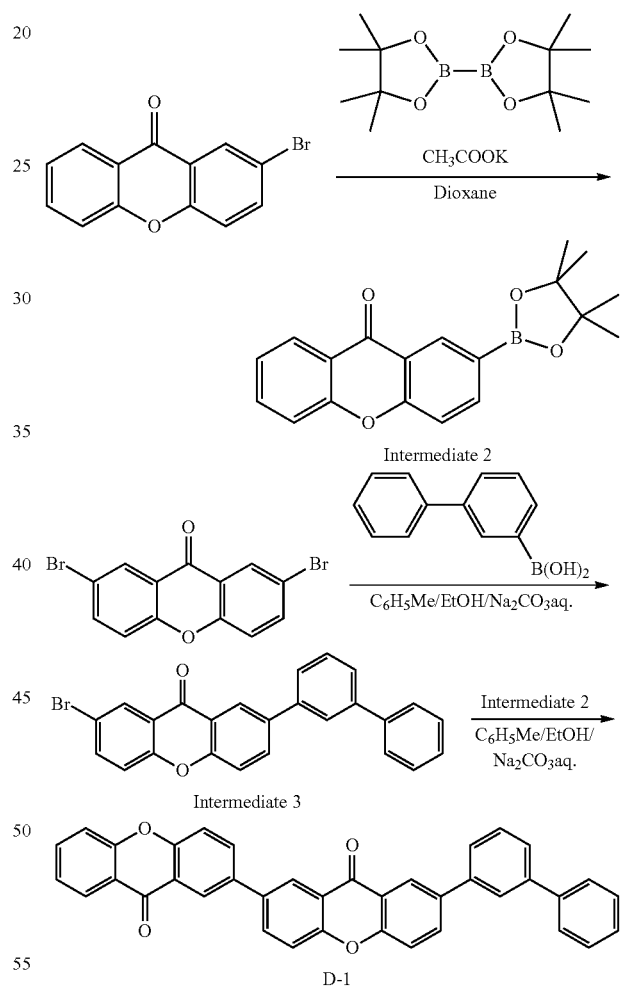

The following reagents and solvents were placed in a 200 mL round-bottomed flask.
2-Bromoxanthone: 5.0 g (18 mmol)
Bis(pinacolato)diboron: 5.5 g (22 mmol)
[1,1'-Bis(diphenylphosphino)ferrocene]palladium(II) dichloride dichloromethane adduct: 0.74 g (0.91 mmol)
Potassium acetate: 3.2 g (33 mmol)
Dioxane: 40 mL The reaction solution was refluxed for 3 hours under heating and stirring in nitrogen. Upon completion of the reaction, the precipitated salt was removed by filtration. The solvent in the obtained filtrate was distilled away at a reduced pressure. The precipitated solid was purified with a silica gel column (ethyl acetate:heptane=1:2). As a result, 5.1 g (yield: 87%) of intermediate 2 was obtained.

Intermediate 3 was obtained by the same method for synthesizing intermediate 1 in Example 3 except that the phenyl boronic acid used in synthesis of intermediate 1 in Example 3 was changed to 3-biphenylboronic acid.

Example Compound D-1 was obtained by the same method for synthesizing Example Compound A-7 except that the 2-bromoxanthone used in synthesizing Example Compound A-7 of Example 1 was changed to intermediate 3 and the boronic acid ester derivative 1 was changed to intermediate 2 (1.1 equivalents relative to intermediate 3).

$M^+$ of this compound, 542.2, was confirmed by MALDI-TOF MS.

Example 6

Synthesis of Example Compound D-2

[Chem. 24]

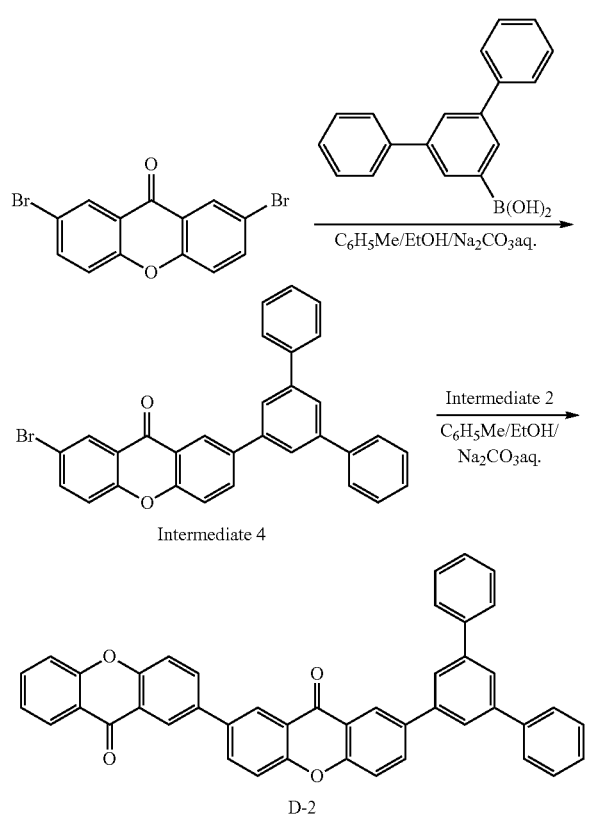

Intermediate 4 was obtained by the same method for synthesizing intermediate 1 in Example 3 except that phenylboronic acid used in synthesis of intermediate 1 in Example 3 was changed to 3,5-diphenylphenylboronic acid.

Example Compound D-2 was obtained by the same method for synthesizing Example Compound D-1 in Example 5 except that intermediate 3 used in synthesis of Example Compound D-1 in Example 5 was changed to intermediate 4.

$M^+$ of this compound, 618.2, was confirmed by MALDI-TOF MS.

Example 7

Synthesis of Example Compound D-7

[Chem. 25]

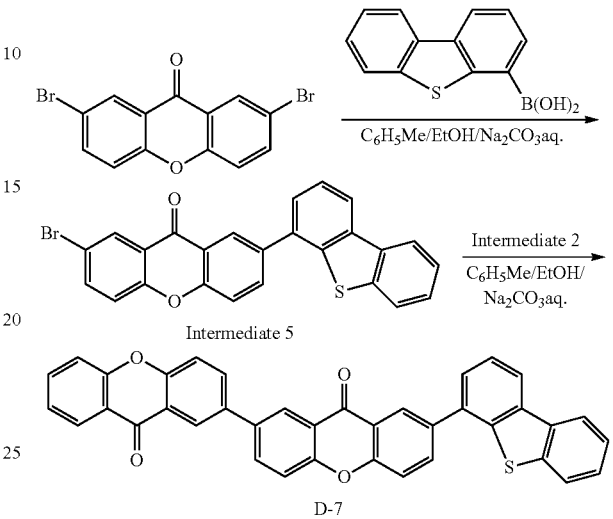

Intermediate 5 was obtained by the same method for synthesizing intermediate 1 in Example 3 except that phenylboronic acid used in synthesis of intermediate 1 in Example 3 was changed to dibenzothiophen-4-ylboronic acid.

Example Compound D-7 was obtained by the same method for synthesizing Example Compound D-1 in Example 5 except that intermediate 3 used in synthesis of Example Compound D-1 in Example 5 was changed to intermediate 5.

$M^+$ of this compound, 572.1, was confirmed by MALDI-TOF MS.

Example 8

Production of Organic Light-Emitting Device

In this example, an organic light-emitting device having a structure including an anode, a hole transport layer, an emission layer, a hole blocking layer, an electron transport layer, and a cathode formed in that order on a substrate was produced by the following method.

Indium tin oxide (ITO) was sputter-deposited on a glass substrate to form a film 120 nm in thickness functioning as an anode. This substrate was used as a transparent conductive support substrate (ITO substrate). Organic compound layers and electrode layers below were continuously formed on the ITO substrate by vacuum vapor deposition under resistive heating in a $10^{-5}$ Pa vacuum chamber. The process was conducted so that the area of the opposing electrodes was 3 mm².

Hole transport layer (40 nm) HTL-1
Emission layer (30 nm), host material 1: I-1, host material 2: none, guest material: Ir-1 (10 wt %)
Hole blocking (HB) layer (10 nm) A-7
Electron transport layer (30 nm) ETL-1
Metal electrode layer 1 (0.5 nm) LiF
Metal electrode layer 2 (100 nm) Al

[Chem. 26]

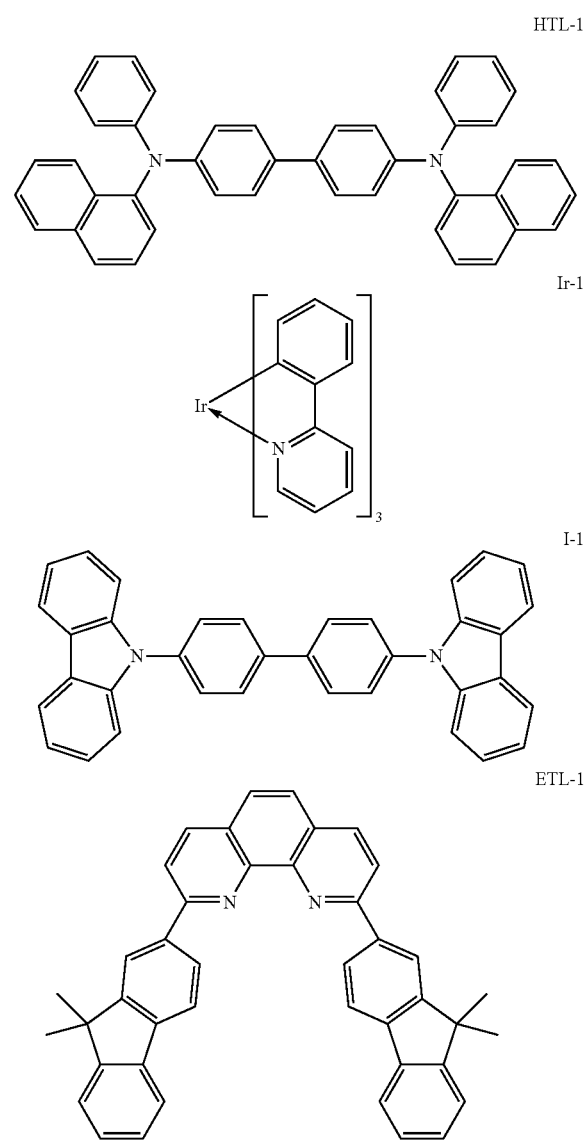

A protective glass plate was placed over the organic light-emitting device in dry air to prevent deterioration caused by adsorption of moisture and sealed with an acrylic resin adhesive. Thus, an organic light-emitting device was produced.

The current-voltage characteristic of the organic light-emitting device was measured with 2700 series ammeter produced by Keithley Instruments Inc., and the emission luminance was measured with BM7-fast produced by TOPCON CORPORATION. A voltage of 5.0 V was applied to the ITO electrode functioning as a positive electrode and an aluminum electrode functioning as a negative electrode. The emission efficiency was 56 cd/A and emission of green light with a luminance of 1920 cd/m² was observed. The CIE color coordinate of the device was (x, y)=(0.34, 0.62).

Examples 9 to 19

Devices were produced as in Example 8 but with different hole blocking material (HB material), host material 1 and host material 2 (15 wt %) of emission layers, and guest material (10 wt %). The devices were evaluated as in Example 8. The emission efficiency, applied voltage, and color of emission at 2000 cd/m² are shown in Table 3.

TABLE 3

| Example No. | HB material | Host material 1 | Host material 2 | Guest material | Emission efficiency (cd/A) | Voltage (V) | Emission color |
|---|---|---|---|---|---|---|---|
| 9 | A-7 | I-1 | A-7 | Ir-1 | 61 | 5.0 | Green |
| 10 | A-7 | I-5 | None | Ir-13 | 10 | 6.6 | Blue |
| 11 | A-6 | I-1 | None | Ir-1 | 53 | 5.4 | Green |
| 12 | A-6 | I-2 | A-6 | Ir-1 | 58 | 5.2 | Green |
| 13 | C-1 | I-2 | None | Ir-1 | 56 | 5.2 | Green |
| 14 | C-1 | I-1 | D-1 | Ir-3 | 63 | 4.9 | Green |
| 15 | D-1 | I-1 | None | Ir-1 | 52 | 5.5 | Green |
| 16 | D-1 | I-3 | D-1 | Ir-4 | 56 | 5.6 | Green |
| 17 | D-2 | I-4 | None | Ir-15 | 12 | 6.5 | Blue-Green |
| 18 | D-2 | I-5 | D-7 | Ir-15 | 16 | 6.4 | Blue-Green |
| 19 | A-1 | I-6 | A-1 | Ir-13 | 11 | 6.8 | Green |

The results show that the when the xanthone compound of the present invention is used as an electron transport material or an emission layer material of a phosphorescence-emitting device, high emission efficiency can be achieved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-247857, filed Nov. 4, 2010, which is hereby incorporated by reference herein in its entirety.

REFERENCE SIGNS LIST

8 TFT element
11 anode
12 organic compound layer
13 cathode

The invention claimed is:
1. An organic light-emitting device comprising:
a pair of electrodes; and
an organic compound layer disposed between the pair of electrodes, wherein the organic compound layer contains a xanthone compound represented by general formula [1]

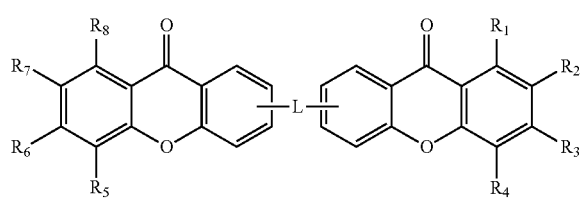

where $R_1$ to $R_8$ are each independently selected from a hydrogen atom an alkyl group having 1 to 4 carbon atoms, a substituted or unsubstituted phenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted chrysenyl group, a substituted or unsubstituted dibenzofuranyl group, and a substituted or unsubstituted dibenzothienyl group; and L represents a single bond, a substituted or unsubstituted divalent benzene, a substituted or unsubstituted divalent biphenyl, a substituted or unsubstituted divalent terphenyl, a substituted or unsubstituted divalent naphthalene, a substituted or unsubstituted divalent phenanthrene, a substituted or unsubstituted divalent fluorene, a substituted or unsubstituted divalent triphenylene, a substituted or unsubstituted divalent chrysene, a substituted or unsubstituted divalent dibenzofuran, or a substituted or unsubstituted divalent dibenzothiophene, wherein the benzene, the biphenyl, the terphenyl, the naphthalene, the phenanthrene, the fluorene, the triphenylene, the chrysene, the dibenzofuran, and the dibenzothiophene may have an alkyl group having 1 to 4 carbon atoms as a substituent.

2. The organic light-emitting device according to claim 1 wherein the organic compound layer has an emission layer, and the emission layer contains the xanthone compound.

3. The organic light-emitting device according to claim 1, wherein
the organic compound layer includes an emission layer, an electron transport layer in contact with the emission layer, and an electron injection layer that transports electrons supplied from one of the electrodes to the electron transport layer, and
at least one of the electron transport layer and the electron injection layer contains the xanthone compound.

4. The organic light-emitting device according to claim 2, wherein
the emission layer contains a host material and a guest material,
the host material is the xanthone compound, and
the guest material is an iridium complex.

5. A display apparatus comprising:
a plurality of pixels each including
the organic light-emitting device according to claim 1 and
a switching element coupled to the organic light-emitting device.

6. An image input apparatus comprising:
a display unit configured to output an image; and
an input unit configured to input image data,
wherein the display unit includes a plurality of pixels and each of the pixels includes the organic light-emitting device according to claim 1 and a switching element coupled to the organic light-emitting device.

7. An apparatus comprising a substrate and the organic light emitting device according to claim 1.

8. A lighting apparatus comprising the organic light-emitting device according to claim 1.

9. An electrophotographic image-forming apparatus comprising an exposure light source, the exposure light source comprising the organic light-emitting device according to claim 1.

10. An exposure light source of an electrophotographic image-forming apparatus comprising the organic light-emitting device according to claim 1.

11. A device comprising:
a pair of electrodes; and
an organic compound layer disposed between the pair of electrodes,
wherein the organic compound layer contains a xanthone compound represented by general formula [1]

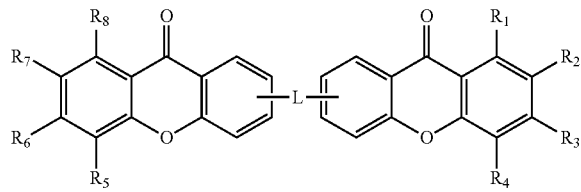

[1]

where $R_1$ to $R_8$ are each independently selected from a hydrogen atom an alkyl group having 1 to 4 carbon atoms, a substituted or unsubstituted phenyl group, a substituted or unsubstituted naphthyl group, a substituted or unsubstituted phenanthryl group, a substituted or unsubstituted fluorenyl group, a substituted or unsubstituted triphenylenyl group, a substituted or unsubstituted chrysenyl group, a substituted or unsubstituted dibenzofuranyl group, and a substituted or unsubstituted dibenzothienyl group; and L represents a single bond, a substituted or unsubstituted divalent benzene, a substituted or unsubstituted divalent biphenyl, a substituted or unsubstituted divalent terphenyl, a substituted or unsubstituted divalent naphthalene, a substituted or unsubstituted divalent phenanthrene, a substituted or unsubstituted divalent fluorene, a substituted or unsubstituted divalent triphenylene, a substituted or unsubstituted divalent chrysene, a substituted or unsubstituted divalent dibenzofuran, or a substituted or unsubstituted divalent dibenzothiophene, wherein the benzene, the biphenyl, the terphenyl, the naphthalene, the phenanthrene, the fluorene, the triphenylene, the chrysene, the dibenzofuran, and the dibenzothiophene may have an alkyl group having 1 to 4 carbon atoms as a substituent.

* * * * *